(12) United States Patent
Hau

(10) Patent No.: US 6,248,718 B1
(45) Date of Patent: *Jun. 19, 2001

(54) LESION-DIRECTED DRY DOSAGE FORMS OF ANTIBACTERIAL AGENTS FOR THE TREATMENT OF ACUTE MUCOSAL INFECTIONS OF THE ORAL CAVITY

(75) Inventor: Kee Hung Hau, Woodbridge, CT (US)

(73) Assignee: Atlantic Biomed Corporation (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/376,950

(22) Filed: Aug. 18, 1999

(51) Int. Cl.$^7$ .......................... A61K 31/70; A61K 31/65; A61K 33/32; A61K 33/34

(52) U.S. Cl. ................ 514/29; 514/31; 514/39; 514/152; 514/192; 514/200; 424/641; 424/653; 424/692

(58) Field of Search .................. 514/29, 31, 39, 514/152, 192, 200; 424/641, 653, 692

(56) References Cited

U.S. PATENT DOCUMENTS

| | | | |
|---|---|---|---|
| 4,177,254 | 12/1979 | Khan et al. | 424/16 |
| 4,748,022 | 5/1988 | Busciglio | 424/195 |
| 5,049,384 | 9/1991 | Kim | 424/405 |
| 5,476,667 | 12/1995 | Kristensen et al. | 424/489 |
| 5,503,845 | 4/1996 | Goede et al. | 424/464 |
| 5,534,262 | 7/1996 | Dobrotvorsky et al. | 424/464 |
| 5,637,616 | 6/1997 | Sharpe et al. | 514/562 |
| 5,679,339 | 10/1997 | Keith et al. | 424/85.2 |
| 5,981,499 | 11/1999 | Hau | 514/29 |

FOREIGN PATENT DOCUMENTS

| | | |
|---|---|---|
| 743895 | 10/1966 | (CA) . |
| WO 95/22983 | 8/1995 | (WO) . |
| WO 96/24342 | 8/1996 | (WO) . |
| WO 9702021 | 1/1997 | (WO) . |

OTHER PUBLICATIONS

Adkinson, N. F., "Risk Factors for Drug Allergy," J. Allergy Clin. Immul., vol. 74, pp. 567–572 (Oct. 1984).
Allergy Principles and Practice, eds. Middleton, E., Jr., Reed, C.E., et al., vol. II, 4th Edition, Mosby–Year Book, Inc., St. Louis, 1993, pp. 1611–1612.
Anderson, John, "Allergic Reactions to Drugs and Biological Agents," JAMA, vol. 268, No. 20, chapter 7, pp. 2845–2857 (1992).
Diagnostic Bacteriology, eds. Schaub, I.G., Foley, M. K. et al., 5th Edition, C.V. Mosby Co., St. Louis, pp. 193–203 (1958).
Fleming, A., "On the Antibacterial Action of Cultures of a Penicullium, with Special Reference to their Use in the Isolation of B. Influenze," Brit, J. Exper. Pathol., vol. X, No. 3, pp. 226–236 (1929).

Graykowski, et al., "Periadenitis aphthae: clinical and histopathologic aspects of lesions in a patient and of lesions producted in rabbit skin,"J. Amer. Dental Association, vol. 69, pp. 118–126 (1964).
Graykowski, et al., "Recurrent Aphthous Stomatisis," JAMA, vol. 196, No. 7, pp. 637–644 (1966).
Green, et al., "Report of the Penicillin Study Group—American Academy of Allergy," J. Allergy Clin. Immunol., vol. 48, No. 6, pp. 331–343 (1971).
Guillemot et al, "Low Dosage and Long Treatment Duration of B–Lactam," JAMA, vol. 279, No. 5, pp. 365–370 (1998).
Idsoe et al, "Nature and Extent of Penicillin Side–reactions, with Particular Reference to Fatalities from Anaphylactic Shock," Bull. WHO, vol. 38, pp. 159–188 (1968).
Klaus, et al., "Penicilloyl–Specific Serum Antibodies in Man," J. Cerontology, vol. 28, No. 3, pp. 312–316 (1973).
Levine et al., "Benzylpenicilloyl–Specific Serum Antibodies to Penicillin in Man," J. Immunology, vol. 96, No. 4, pp. 719–726 (1966).
Mecical Mycology, eds. K.J. Kwon–Chung and J.E. Bennett, Lea & Febiger, Philadelphia, pp. 281–282 (1992).
Nathan et al., "Outcomes Study in 3 Private Practices Show that Immunotherapy is Effective in Atopic Patients with Sinusitis," Annals of Allergy, Asthma & Immunology, vol. 82, p. 92 (Abstract) (1999)/.
Odds, et al., "Candida concentrations in the vagina and their association with signs and symptoms of vaginal candidosis," J. Med. Vet. Mycology, vol. 26, pp. 277–283 (1988).
Salvaggio, et al., "A Comparison of the Immunologic Responses of Normal and Atopic Individuals to Intranasally Administered Antigen," J. Allergy, vol. 35, No. 1, pp. 62–69 (1964).
Schrag, et al., "Reducing Antibiotic Resistance," Nature, vol. 381, pp. 120–121 (1996).
Shepherd, G., "Allergy to B–Lactam Antibiotics," Immunology and Allergy Clinics of North America, vol. 11, No. 3, pp. 611–633 (1991).

(List continued on next page.)

*Primary Examiner*—Elli Peselev
(74) *Attorney, Agent, or Firm*—Nash and Titus, LLC

(57) ABSTRACT

The invention provides a medicament for topically treating acute bacterial infections in the oral mucosa, and methods of use. The medicament comprises a dry dosage (such as a troche or powder) of one or more antibacterial agents and, preferably, one or more polyvalent metal compounds. The medicament is directly applied to the site of the infection and dissolves in saliva, within about 5 to about 15 minutes, thereby directly delivering a supratherapeutic dosage of the antibacterial agent to the infected oral tissue. Further, in a preferred embodiment the medicament directly delivers a therapeutically high concentration of a polyvalent metal compound in suspension to the infected area, thereby forming a protective barrier over the infected oral tissue.

18 Claims, 17 Drawing Sheets

(17 of 17 Drawing Sheet(s) Filed in Color)

OTHER PUBLICATIONS

Sullivan et al., "Desensitizationof patients allergic to penicillin using orally admistered B–Lactan antibiotics," J. Allergy Clin, Immunol., vol. 69, No. 3, pp. 275–282 (1982).

"Penicillin G Potassium," USP 23 NF 18, p. 1168, 1995.

"Dissolution," USP 23 NF 18, pp. 1791–1793, 1995.

VanArsdel, P., "Classification and Risk Factors for Drug Allergy," Immunology and Allergy Clinics of North America, vol. 11, No. 3, pp. 475–493 (1991).

Oxford Textbook of Pathology, vol. 1, Principles of Pathology, ed. McGee, J., Isaacson, P., Wright, N., Oxford University Press, Oxford, p. 374 (1992).

Dispensatory of the United States of America, 25th Ed., Edited by Osol A. and Farrar, G., published by J.B. Lippincott Co., Philadelphia (1955), pp. 1006–1008.

Oral Pathology, Edited by Thoma, K. and Goldman, H., published by C.V. Mosby Co. (1960), pp. 1066–1069.

The Use of Antibiotics, Edited by Kucers, A. and Bennett, N.; published by J.B. Lippincott Co., Philadelphia (1987), pp. 16–18.

Gastrointestinal Disease, Pathophysiology/Diagnosis/Management, vol. 1, Edited by Sleisenger, M. and Fordtran, J., published by W.B. Saunders Co., Philadelphia (1993), p. 273.

Nelson Textbook of Pediatrics, 15th Edition, Edited by Nelson, W., published by W.B. Saunders Co., (1996) pp. 1888–1889.

Goodman and Gilman's The Pharmacological Basis of Therapeutics, 6th Edition, published by Macmillan Publishing Co., Inc., New York (1980), pp. 953, 1136 and 1137.

The Merck Manual of Diagnosis and Therapy, 13th Edition, Edited by Berkow, R. and Talbott, J., published by Merck Sharp and Dohme Research Laboratories, Rahway, New Jersey (1977), pp. 1666–1667.

Ylikontiola et al., "Doxymycine–cyanoacrylate treatment of recurrent aphthous ulcers," Oral Surgery Oral Medicine Oral Pathology Oral Radiology Endod. vol. 83, No. 3, (1997), pp. 329–333.

The Merck Index: an Encyclopedia of Chemicals, Drugs and Biologicals, 11th Edition, Edited by Budavari, S. et al., published by Merck & Co., Inc., Rahway, New Jersey (1989), p. 5572.

Physician's Desk Reference, 41 Edition, publisher Edward R. Barnhart, published by Medical Economics Company, Inc., Oradell, New Jersey (1987), pp. 1170–1171.

Physician's Desk Reference, 52 Edition, published by Medical Economics Company, Inc., Oradell, New Jersey (1998), pp. 3097–3098.

Grzesiak et al., "Shifts in the Concentration of Magnesium and Calcium in Early Porcine and Rat Wound Fluids Activate the Cell Migratory Response," J. Clin, Invest., vol. 95 (1995), pp. 227–233.

Tone et al., "Influence of Zinc Deficiency on Phagocytosis in Mice," Kitasato ARch. of Exp. Med., vol. 64, No. 4 (1991), pp. 263–269.

Rattan et al., "Sucralfate suspension as a treatment of recurrent aphthous stomatitis," Medline Abstract, taken from J. Intern. Med, vol. 236, No. 3 (1994), pp. 341–343.

Campisi et al., "Sucralfate in odontostomatology. Clinical experience," MedLine Abstract, taken from Minerva Stomatol., vol. 46, No. 6 (1997), pp. 297–305.

Mahdi et al., "Efficacy of bioadhesive patches in the treatment of recurrent aphthous stomatitis," MedLine Abstract, taken from J. Oral. Pathol. Med., vol. 25, No. 8 (1996), pp. 416–419.

Merchant et al., "Zince sulfate supplementation for treatment of recurring oral ulcers," MedLine Abstract, taken from South. Med. J., vol. 70, No. 56 (1977), pp. 559–561.

Agren et al., "Selenium, zinc, iron and copper levels in serum of patients with arterial and venous leg ulcers," MedLine Abstract, taken from Acta. Derm. Venereol., vol. 66, No. 3 (1986), pp. 237–240.

Slomiany et al., "Sucralfate affects the susceptibility of Helicobacter pylori to antimicrobial agents", MedLine Abstract, taken from Scand. J. Gastroenterol. Suppl., vol. 210 (1995) pp. 82–84.

al–Assi et al., "Clarithromycin, tetracycline, and bismuth: a new non–metronidazole therapy for Helicobacter pylori infection", MedLine Abstract, taken from Am. J. Gastroenterol, vol. 89, No. 8 (1994), pp. 1203–1205.

Endre, L., "Recurrent aphthous ulceration with zinc deficiency and cellular immune deficiency," MedLine Abstract, taken from Oral. Surg. Oral Med. Oral. Pathol., vol. 72, No. 5 (1991) pp. 559–561.

Greer, et al., "A double–blind study of topically applied 5% amlexanox in the treatment of aphthous ulcers", MedLine Abstract, taken from J. Oral Maxillofac Surg., vol. 51, No. 3 (1993) pp. 243–248.

Phelan, et al., "Major aphthous–like ulcers in patients with AIDS," MedLine Abstract, taken from Oral.Surg. Oral Med. Oral. Pathol., vol. 71, No. 1 (1991) pp. 68–72.

Sunairi et al., "Effects of anti–ulcer agents on antibiotic activity against Helicobacter pylori," MedLine Abstract, taken from Eur. J. Gastroenterol. Hepatol., vol. 6, Suppl. 1 (1994), pp. S121–S124.

Grzesiak et al., "Changes in the concentrations of extracellular MG++ and Ca++ down–regulate E–cadherin and up–regulate alpha 2 beta 1 integrin function, activating keratinocyte migration on type I collagen," MedLine Abstract, taken from J. Invest. Dermatol., vol. 104, No. 5 (1995), pp. 768–774.

Rosch, W., "Therapy of peptic ulcer and chronic gastritis with bismuth salts," MedLine Abstract, taken from Z. Gastroenterol., vol. 25, Suppl. 4 (1987), pp. 34–40.

Cox et al., "Evaluation of intravenous magnesium sulfate for the treatment of hydrofluoric acid burns,"MedLine Abstract, taken from J. Toxicol. Clin. Toxicol., vol. 32, No. 2 (1994), pp. 123–136.

Harris, et al., "Comparative efficacy of injectable calcium magnesium salts in the therapy of hydrofluoric acid burns," MedLine Abstract, taken from Clin. Toxicol., vol. 18, No. 9 (1981), pp. 1027–1032.

Jacobson, et al., "Thalidomide for the treatment of oral aphthous ulcers in patients with human immunodeficiency virus infection. National Institute of Allergy and Infectious Diseases AIDS Clinical Trials Group,"MedLine Abstract, taken from N. Engl. J. Med., vol. 336, No. 21 (1997), pp. 1487–1493.

The United States Dispensatory, 27th Edition, Edited by Osol, A. and Pratt, R., published by J.B. Lippincott Co., Philadelphia (1973) p. 877.

Thoma's Oral Pathology, vol. 1, edited by Gorlin, R. and Goldman, H., published by C.V. Mosby Co., St. Louis, (1970), pp. 394–399.

AHFS Drug Information, edited by McEvoy, G., published by Authority of the Board of the American Society of Health–System Pharmacists, (1997), pp. 251–252.

Spark, R., "Fatal Anaphylaxis Due to Oral Penicillin," Amer. J. Clin. Pathol., vol. 56 (1971) pp. 407–411.

Chain, et al., "Penicillin as a Chemotherapeutic Agent," Lancet, vol. 2 (1940), pp. 226–228.

Abraham, et al., "Further Observations on Penicillin," Lancet, vol. 2 (1941), pp. 177–189.

Weinstein, et al., "Clinical and Bacteriologic Studies of the Effect of "Massive" Doses of Penicillin G on Infections Caused by Gram–Negative Bacilli," New Engl. J. Med., vol. 271, No. 11 (1964), pp. 525–532.

LESION-DIRECTED DRY DOSAGE FORMS OF ANTIBACTERIAL AGENTS FOR THE TREATMENT OF ACUTE MUCOSAL INFECTIONS OF THE ORAL CAVITY

BACKGROUND OF THE INVENTION

Anatomically, the oral cavity is composed of two parts, the vestibule and the mouth cavity proper. The vestibule is limited by the reflections of the mucous membranes, also referred to as mucosa(e), from the lips and cheeks to the gums covering the upper and lower alveolar arches respectively. The mouth cavity proper is bounded laterally and ventrally by the alveolar arches with the their contained teeth; dorsally, it communicates with the pharynx. It is roofed in by the hard and soft palates, while the greater part of the floor is formed by the tongue, the remainder by the reflection of the mucosae from the sides and under surface of the tongue to the gum lining the inner aspect of the mandible. Gingiva(e), the gum, is composed of dense, fibrous tissue which is covered with vascular mucous membrane and connected to the periosteum on the edges of the alveolar processes of the mandible and maxilla. At the neck of the teeth, the fibrous tissue of the gingiva is continuous with the periosteum lining the alveoli. Except the teeth, the entire oral cavity is lines by mucosae with a squamous epithelium lining on the surface. Inflammation of the oral mucosae which may involve the buccal and labial mucosa, palate, tongue, floor of the mouth, and the gingivae, including the periodontal pockets is referred to as stomatitis.

The mucosae of the oral cavity are normally colonized by a large and diverse microbial flora. These bacteria are constantly interacting with the host and with each other in competition for survival. The number of microorganisms in 1 ml of human saliva swallowed is approximately 100 million. About 100 billion bacteria are produced in a human oral cavity in about one liter of saliva swallowed per day. There are over 200 different species of microorganisms that can be isolated from the oral cavity. But the composition of these so-called normal floras may change according to the environment and may differ from location to location in the mouth.

Certain genera, such as the Streptococcus, Actinomyces, Neisseria, and Bacteroides appear to be found in the oral cavity of all humans in high numbers. These are referred to as "indigenous flora."

Some microbes, for example, Lactobacillus species, *Streptococcus mutans, Porphyromonas gingivalis, Actinobacillus actinomycetemcomitans*, diphtheroids, Nocardia, fusiform bacilli and spirochetes are nearly always present, but in low numbers (less than 1%). These are referred to as "supplemental flora", but may become indigenous if the environment changes.

"Transient flora" comprise organisms "just passing through" the host. They may be present in food or drink and may be established temporarily in the mouth, but normally cannot persist in the crowded oral environment, and quickly disappear. These include Enterobacteriaceae, Staphylococcus, yeasts, Candida and other fungi.

There normal floras usually exist in symbiotic and amphibiotic patterns in the mouth, and are normally saprophytic in nature. However, they are quite capable of assuming pathogenic tendencies, thus either precipitating or aggravating disease, and are referred to as opportunistic pathogens.

An intact oral mucosa is a definite barrier to bacterial invasion. However, should this shield be broken or penetrated, bacteria or their products may enter the underlying connective tissue and grow rapidly to infectious levels. Examination of the bacterial population in the various types of oral mucosal infections has not identified a single group of microbes which can be consistently associated with the diseases. Aerobic streptococci, facultative streptococci, numerous filamentous forms (e.g, Actinomyces), diphtheroids, Gram-negative diplococci (Neisseria), fusiform bacilli, spirochetes, and bacteroides have all been described in the lesions of various oral mucosal infections with or without a concomitant observable ulceration. Any single one of these microorganisms is probably not pathogenic when introduced alone into the healthy exposed underlying tissues not covered by an intact protective mucosa. But working in combination and growing in concert, they can cause and perpetuate serious tissue damages. During the acute inflammatory stage of the bacterial infection, a large number of bacterial endotoxins and exotoxins are released from the living or dead microbes. These toxins may cause increase in vascular permeability, increase in intravascular hydrostatic pressure, outward passage or plasma fluids, release of histamine, heparin and serotonin from the tissue mast cells, which further mediate vascular engorgement and diffusibility of fluid through the endothelium. The pathological changes associated with the acute inflammation almost invariably transform the infected part of the oral mucosa in to a beefy-red painful swelling with or without grossly observable ulceration or erosion. Regardless of the etiology which has caused the initial breakdown of the barrier of the intact oral mucosa, bacterial infection in the most important of all the local factors which may delay the normal healing and repair processes of the lesion.

Suppression or elimination of the bacterial population in an infected lesion is the most logical approach of treatment. However, since the microbes in the human mouth are highly complex in variety and very high in number and since the saliva contains numerous enzymes both of host origin and of bacterial origin which may destroy any anti-infective medicines introduced, systemic routes of administering antibacterial agents for the treatment of oral mucosal infections are generally not effective. Systemic administration of antibacterial agents by parenteral injections or by ingestion of the medicaments cannot bring about an effective bacteria-inhibiting concentration of the drug to the site of infection. In the current invention, the inventor introduces a topical dry-dosage form of antibacterial agent(s) to be used as a topical medication in form of a lozenge to bring about a "supratherapeutic" concentration of antibacterial agent(s) to the lesion of infection, to sterilize the local environment periodically four times a day. Under this topical medication, the pain associated with acute inflammation of the oral mucosa subsides in about 48 hours, and minor mucosal ulcers heal completely in about 4 days. Two clinical examples, namely recurrent minor aphthous stomatitis (also known as canker sores) and acute gingivitis (also known as acute periodontal inflammation) are useful illustrations of this approach to treatment of acute mucosal infections.

Small shallow painful mucosal ulcers of the mouth, commonly referred to as aphthous stomatitis, aphthous ulcers, canker ulcers or canker sores in the medical literature, occur in about 20–25% of the general human population and are not contagious. They often appear on the unkeratinized oral mucosal surface of the soft palate, the ventral or lateral tongue, the buccal-labial mucosa, and the floor of the mouth, and usually recur at irregular intervals with single or multiple lesions. They are often covered with a grayish white exudate and surrounded by a hyperemic or erythematous margin, and are highly sensitive, especially to acid food. The size of these ulcers is rarely more than 5 mm in diameter, but can be larger, and coalescence of multiple ulcers may occur. The pain caused by these ulcers may sometimes extend over the entire face. Small canker sores usually heal spontaneously in one to three weeks, but larger ulcers may require months to resolve, often with scarring.

Three main clinical presentations are recognized, namely, minor canker sores (recurrent aphthous stomatitis), major canker sores (recurrent aphthous stomatitis) and herpetiformn ulcers. Minor canker sores account for more than 80% of the recurrent aphthous stomatitis cases. The size of the minor canker ulcers is rarely more than 5 mm in diameter and heal within 10–14 days without scarring. Major canker sores are a rare severe form of recurrent aphthous stomatitis. These lesions are round or oval, may exceed 1 cm, and may approach 3 cm in diameter. These painful ulcers of major canker sores may persist for up to 6 weeks or longer, healing slowly with scarring. Herpetiforrn ulcers are the least common variety, characterized by multiple recurrent crops of small painful ulcers of 1–3 mm in diameter and distributed throughout the oral cavity. As many as 100 ulcers may be present at a given time, and they tend to coalesce to produce large irregular ulcers.

Although aphthous ulcers were described by Hippocrates about 2,500 years ago, the etiology of these lesions is still largely unknown. While a variety of conditions are associated with aphthous ulcers, immunologic status seems to be an important factor in initiating eruptions. A pleomorphic transitional L-form of an (x-hemolytic streptococcus had been suggested to be the causative agent for recurrent aphthous stomatitis (Graykowski, et al., "Recurrent Aphthous Stomatitis", JAMA 196:637–644, 1966; Graykowski, "Periadenitis aphthae: clinical and histopathologic aspects of lesions in a patient and of lesions produced in rabbit skin", J. Amer. Dental Association, 69:118–126, 1964). However, other investigators have failed to confirm this hypothesis. Since α-hemolytic streptococcus is one of the predominant normal inhabitants in the mouth, its role as a specific causative pathogen for canker sores is difficult to establish. Electron microscopic search of the tissue sections of the canker ulcer lesion also has failed to show evidence of an L-form streptococcus. But anaerobic streptococci which are mostly a-hemolytic probably play an important role in all secondary infections in the mouth. In some patients the incidence of the occurrences of canker sores can be definitely correlated with menstrual cycles. In other cases dietary or digestive disturbances seem to be the precipitating factors. Frequently the lesions are brought on or aggravated by nuts, chocolate, and citrus products. Prolonged fever, emotional stress, local trauma, low serum iron or ferritin levels, deficiency of vitamin B,12 or folate, malabsorption in association with celiac or Crohn's disease, food hypersensitivity and drug reaction may also precipitate outbreaks of canker sores.

The first stage of an emerging canker is a vesicle in the stratum granulosum of the mucosal squamous epithelium, produced by intraepithelial edema. ("Oral Pathology", Eds. K. H. Thoma and H. M. Goldman, 5$^{th}$ Edition, The C. V. Mosby Co., St. Louis, 1960, page 1067). The vesicle contains serum and degenerated epithelial cells, with little inflammatory response. However, this stage is rarely noticed, as the painful symptoms of the ulcer do not occur until the vesicle breaks, presenting an area of ulceration which disrupts the normnal epithelium of the mucosa. Once an ulcer forms, the mucosa is no longer protected by an intact epithelium and the raw surface of the ulcer is exposed to microorganisms which normally inhabit the oral cavity. Examples of such microorganisms include lactobacilli, actinomyces, leptotrichiae, non-β-hemolytic streptococci, enterococci, miscellaneous gram-positive cocci, Neisseriae, diphtheroid bacilli, fusiform bacilli, bacteroides, spirochetes, and yeasts. These so-called normal flora microorganisms, when existent in normally balanced proportions, do not usually produce disease in the intact oral mucosa of a healthy person. However, in a debilitated person, for example, a malnourished patient who has had a preceding illness such as measles, scarlet fever, tuberculosis, malignancy, or immunodeficiency, these microbes working in combination can cause a severe form of acute necrotizing ulcerative gingivitis, often referred to a Vincent's gingivitis. Therefore, these microorganisms are also commonly referred to as opportunistic pathogens. While pure cultures are not pathogenic, a mixture of a spirochete, a fusiform bacillus, a vibrio, and an anaerobic streptococcus of the oral flora can produce a characteristic, transmissible infection in experimental animals.

During the development of a canker ulcer, once the vesicle is broken, the opportunistic pathogens quickly destroy the remnants of the local surface barrier of the oral mucosa, causing secondary infection and a dense acute and a chronic inflammatory cell infiltration of the exposed connective tissue of the *lamina propria mucosae* at the crater of the ulcer. The necrotic tissue, fibrinous exudate and the inflammatory cells constitute a yellowish-white membrane often seen clinically covering the base of an ulcer. There is also marked infiltration of the small neurovascular system in the deeper layer of the *lamina propria mucosae* and at the periphery of the ulcer, which may account for the highly sensitive condition of the lesion and pain-inducing neuritis. The process of healing takes place only after the inflammation subsides, followed by re-epithelialization of the ulcer, with or without scarring. (Also see copending application serial number 09/026,901 for a description of the causes and effects of such ulcers. The entire contents of this copending application are incorporated herein by reference)

Since the etiology of canker ulcers is probably multifactorial, and the precipitating conditions are numerous, causative therapy is pointless. The treatment of aphthous stomatitis to date has been palliative, using various measures to lessen the pain, to control secondary infection, and to reduce inflammatory reaction after the painful ulcer is established. The types of treatments have varied over the years according to the therapeutic means available to the practitioners at the time and according to the understandings of the limitations of these types of the treatments at the time. But in general, these types of palliative treatments have met with only limited success.

For example, in the early 1950's, a recommended local treatment of infections of the oral cavity was lozenges of penicillin. The lozenges were prepared by compression of a mixture of amorphous penicillin or benzylpenicillin and dry granules of sucrose, lactose, or a mixture of the two, and suitable binding agents. (See "The Dispensatory of the Unites States of America", 25$^{th}$ Edition, based on the Fifteenth Revision of the Unites States Pharmacopoeia; The Tenth Edition of The National Formulary; The British Pharmacopoeia, 1953; The First Edition of the International Pharmacopoeia, Volumes I and II, edited by A. Osol and G. E. Farrar and published by J. B. Lippincott Co., Philadelphia, 1955, pages 1007–08) Each lozenge weighed about 1 gram and contained not less than 90.0% of the prescribed or stated number of Units of penicillin. If the quantity was not specified, lozenges containing about 1000

Units (an equivalent of 0.625 mg of penicillin G) were dispensed. Although these lozenges were not specified for the topical treatment of canker ulcers, they were recommended to be employed as a topical medication for the treatment of infections in the mouth and throat. The lozenges were designed to disintegrate slowly, releasing penicillin over a period of 45 to 60 minutes, after which another lozenge was inserted, with this process continuing for 24 hours, except during meals.

However, this topical treatment of aphthous ulcers with penicillin lozenges proved ineffective and was abandoned. Furthermore, as recently as 1980, the use of penicillin for topical applications to mucous membranes and skin was not advised, as such applications were described as ineffective and likely to produce hypersensitivity. (See "The Pharmacological Basis of Therapeutics", Eds. Gilman Goodman, and Gilman, p.1136.) As a result, this type of treatment for aphthous stomatitis was not included in later teachings and in the later editions of pharmacopoeia.

In the most recent medical texts, recommended types of treatment for canker sores include a potent glucocorticoid ointment mixed with an equal volume of Orabase™ (active ingredient: mineral oil; available from Bristol-Myers Squibb of Canada), analgesics, topical anesthetics (such as viscous lidocaine hydrochloride), various hygienic antiseptic mouth rinses, and a topical tetracycline mouthwash four times a day for seven days. (See "Gastrointestinal Disease, Pathophysiology/Diagnosis/Management", $5^{th}$ Edition, ed. by M. H. Sleisenger and J. S. Fordtran, published by W. B. Saunders Co., Philadelphia, 1993, page 273; and "The Nelson Textbook of Pediatrics", $15^{th}$ Edition, ed. R. E. Berhman, R. M. Kliegman and A. M. Arvin, published by W. B. Saunders Co., Philadelphia, 1996, page 1889). However, potent glucocorticoid ointments and systemic therapy with corticosteroids are known to suppress the local and systemic immunity of the body, paving the way to other complications, such as even more severe systemic bacterial or fungal infections. Large doses of corticosteroids impair the healing response in experimental animals. Such steroids have been reported to have adverse effects on epithelial regeneration, the proliferation of fibroblasts, and the synthesis of the extracellular matrix. ("Oxford Textbook of Pathology", Vol. 1, ed. J. McGee et al., Oxford University Press, 1992, page 374) The end result of using steroids to treat an infected wound is likely to delay wound healing.

Therefore, these recommended types of treatment for canker ulcers are not commonly prescribed by the practitioners although steroids may suppress the inflammatory response and reduce the degree of ulcer pain symptomatically. More recently, a paste containing 5% of amlexanox has been approved for the topical treatment of canker sores (marketed under the name Aphthasol™), which is listed in the 1998 edition of the Physician's Desk Reference. According to the data published in the Physician's Desk Reference, topical application of the Aphthasol Oral Paste to the canker sore on the average accelerates complete healing of the canker ulcer and complete ulcer pain relief by 0.7 days. Such a treatment is interpreted as "minimally effective".

Thalidomide therapy for oral aphthous ulcers is effective in some HIV-infected patients, though the adverse effects of this teratogenic drug limit its usefulness in general. Topical treatment with tetracycline suspensions or nystatin suspensions, as well as systemic therapy with penicillin, are commonly employed. A drawback to oral antimicrobial rinses and suspensions is their inability to present high enough (supratherapeutic) concentrations of the active drugs in the immediate vicinity of the ulcers to suppress the growth of the pathogens which have contributed to and continue to perpetuate the infection. For example, one protocol requires patients to hold 250 mg of tetracycline in 5–10 mg/ml suspension in the mouth for 2 to 5 minutes to coat the ulcers, then suggests swallowing the remaining liquid. This treatment is often impractical, especially for use in children. Tetracycline oral suspensions are available commercially in concentrations from about 5 mg/ml to about 10 mg/ml. Supratherapeutic concentrations of, for example, 500 mg/ml are not achievable with these solutions. Likewise, topical combination treatments utilizing pastes of crushed tetracycline tablets (150 mg in 1 ml of saline) and tissue adhesive agents, such as cyanoacrylate, cannot achieve such high levels of antibiotic. Besides, this type of treatment must be performed by a dentist.

Acute gingivitis, or acute periodontal inflammation, also has a complex etiology, including local environmental factors and systemic disturbances. The most important initial factor in causing periodontal diseases is the bacterial plaque which is a soft, sticky, mucilaginous form that accumulates on the teeth, particularly on their cervical portions. It contains adherent mucin, foodstuffs, cellular debris, and a variety of microorganisms, both living and dead. Plaque may calcify to form calculus, and newly forming plaque, overlying the calculus, in turn undergoes mineralization. The process is thus repetitive. The bacteria observed in a plaque are those of oral floras, including aerobic and anaerobic streptococci, staphylococci, lactobacilli, Actinomyces, Nocardia, bacteroides, fusiform bacilli and spirochetes. The bacterial plaque tends to progress and eventually destroys the normal anatomical relationship at the junction between the gingival mucosa and the teeth, leading to the formation of periodontal pocket. Once formed, the periodontal pocket in turn alters the local environment, becoming a locus for debris, calculus, bacteria and food. Effect becomes cause.

Under a variety of conditions, such as when there is inadequate oral hygiene or when there is a minor trauma causing breakdown of the intact protective squamous epithelium of the gum, the opportunistic bacteria may gain access into the connective tissue, to initiate a painfuil acute periodontal infection, acute gingivitis. The standard treatment has been to administer systemic antibacterial agents via parenteral injections or oral ingestion for gastrointestinal absorption with slow response, usually taking about seven to ten days to gain complete relief of pain.

An obstacle to inhibiting microbial proliferation is the fact that many bacteria arc resistant to the concentrations of antibiotics attainable in blood or in tissues during medication. This property of drug resistance may be natural or acquired. However, the growth of many "resistant" microorganisms can be inhibited in vitro by increasing the concentrations of the antibiotic to a supratherapeutic level that is not safely attainable in blood or in tissue fluids via conventional gastrointestinal absorption or intramuscular and intravenous injections. For example, Gram-negative bacilli are generally regarded as being resistant to penicillin G, even at the concentration of 16 mcg/ml which is accepted as the average peak blood level after an intravenous injection of 500 mg of penicillin G. However, if a high concentration of penicillin G is used (such as, for instance, 740 mcg/ml) as the cut-off minimum inhibition concentration (MIC) for classifying sensitive and resistant strains, many Gram-negative bacilli (including, for instance, Salmonella, Shigella, most Escherichia coli strains, all Proteus mirabilis strains and most Bacteroides strains) would fall into the "sensitive" category. Needless to say, in clinical practice, drug toxicity and rapid renal clearance usually prevent this substantial level of antibiotic being achieved in human blood and tissue fluids via systemic oral or parenteral medication.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIG. 1 Saliva, 0.1 ml, from a normal adult. Inoculated on the surface of a 5% sheep blood agar plate and incubated aerobically in an atmosphere containing 5% carbon dioxide at 37° C. for 18 hours. The culture is dominated by colonies of Neisseriae with those of non-β-hemolytic streptococci scattered in between.

FIG. 3 Saliva, 0.1 ml, from a normal adult (aliquot of the same sample used for culture shown in FIG. 1 ). Inoculated on the surface of a 5% sheep blood agar plate and incubated anaerobically at 37° C. for 18 hours. The culture is dominated by colonies of non-β-hemolytic streptococci with those of Neisseriae scattered in-between.

FIG. 4 Gram-stain of the culture on plate of FIG. 3, showing mostly Gram-positive short-chain-forming cocci and a few Gram-negative diplococci scattered in-between.

SUMMARY OF THE INVENTION

Figure 1:
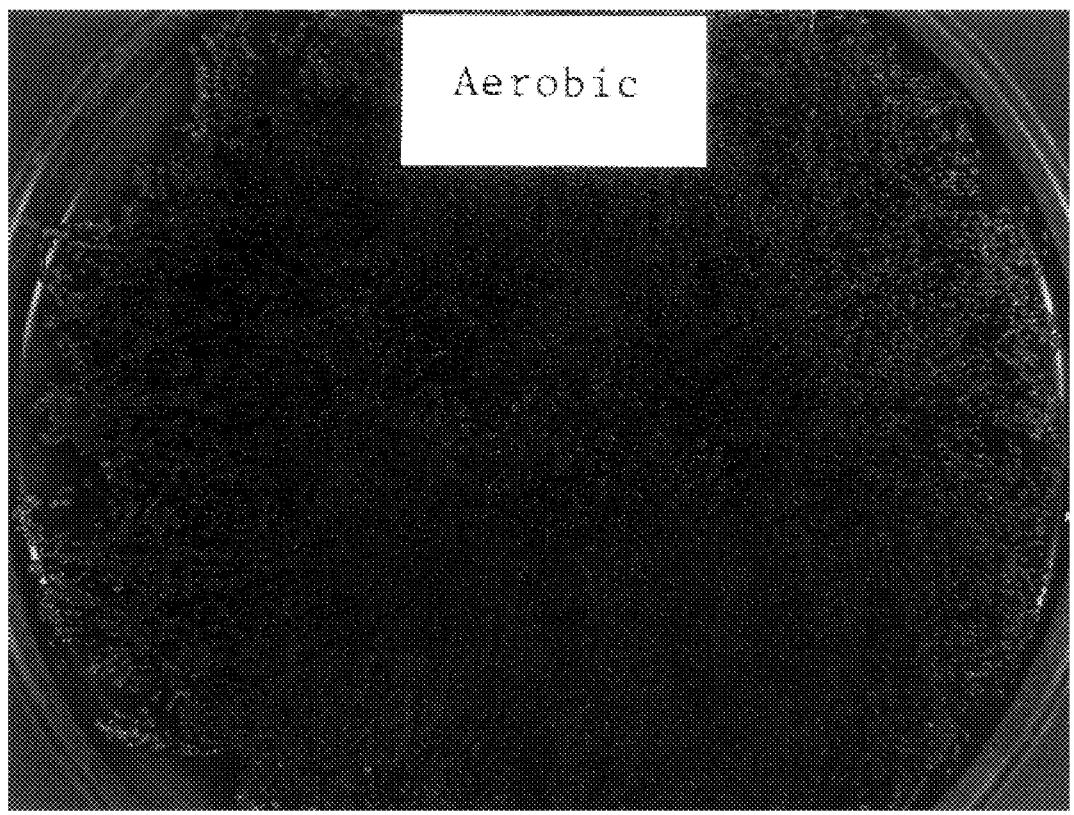

With the above in mind, an object of this invention is to provide an effective topical treatment for all types of acute bacterial infections of the oral mucosa, This is achieved by a novel medicament which includes a dry dosage of an antibacterial agent which, when applied topically, delivers directly to the site of the infection a supratherapeutic level of antibacterial agent. The term "supratherapeutic level of dosage" denotes a dosage of the antibacterial agent which is substantially higher than dosage levels achieved when the antibacterial agent is delivered to the site of the infection through blood by conventional gastrointestinal absorption, intramuscular or intravenous injection of the antibacterial agent. For instance, to effectively inhibit the growth of bacteria causing infection, the dosage should be sufficient to attain a concentration of at least 1 mg/ml, and preferably at least 2 mg/ml, of antibacterial agent in the human saliva.

The composition may be in the form of a powder, or preferably, a troche.

The antibacterial agent may be one of the known antibiotics such as penicillins, beta-lactam antibiotics, tetracyclines, aminoglycosides, cephalosporins, macrolides, vancomycin, bacitracin, chloramphenicol, and their salts, and mixtures thereof. The antibacterial agent may also be a non-antibiotic, such as quinolones, sulfonamides, nitrofurans and their salts, and mixtures thereof.

Preferably, the medicament includes an effective amount of a salt or oxide of a polyvalent metal compounds such as magnesium, zinc, calcium, aluminum, bismuth, titanium and copper and mixtures thereof. Ideally, the polyvalent metal compound is delivered to the site of the infection in a concentration sufficiently high that, when the medicament is dissolved in saliva at the site of the infection, it forms a protective barrier over the raw surface of the infection.

Along these lines, another object of the invention provides a method of treating mucosal infections comprising directly topically administering the medicament composition containing a dry dosage of antibacterial agent, or preferably, a composition containing antibacterial agent and polyvalent metal ions.

These and other objects of the invention will be further characterized in the detailed description of the invention provided hereinafter.

DETAILED DESCRIPTION OF THE INVENTION

As mentioned above, the dry dosage topical medication of this invention comprises a supratherapeutically high dosage of one or more antibacterial agents. It is believed that these medicaments and the methods of their use can achieve a periodic total growth inhibition of the bacteria that constitute the overwhelming majority of the microbial population in the saliva that can be cultured on blood agar plates and that are observed routinely in a clinical laboratory. By achieving periodic total growth inhibitions of the overwhelming opportunistic flora, the mucosal infection perpetuated by the pathogens will be put under control.

The medicament and its method of administration can be effective against most types of acute mucosal infections. The so-called normal oral flora includes a wide variety of microbes that are normally saprophytic, but are capable of assuming pathogenic tendencies that can precipitate or aggravate infection. Examples of such bacteria found in the periodontal pocket include aerobic streptococci, facultative streptococci, numerous filamentous forms (e.g., *Actinomyces naeslandi*), Gram-negative diplococci (e.g., Neisseria), fusospirochetal types, and bacteroides (e.g., *Bacteroides melaninogenicus*). Under favorable conditions, these bacteria, and others, can grow rapidly in combination and cause or aggravate infection. Specific types of infections that can be caused or aggravated by these opportunistic pathogens include, periodontal infections and other types of stomatitis. The medicament and methods of this invention contemplate effective treatment, or at least result in some significant level of inhibition, of these infections or other infections caused by oral flora. In addition, a dentist may use the medicament prophylactically, to prevent infection in cases where conditions are known to be favorable for infection (such as following oral surgery).

In general, this dry form of medication is composed of fine medicinal powders of an antibacterial agent, which may be compressed as troches or kept in powder form. The antibacterial agent may be any of the antimicrobial agents produced by fungi, bacteria, plants, by chemical synthesis, or by genetic engineering technology, which have bacteriocidal or bacteriostatic activities in aqueous solutions against opportunistic flora of the human oral cavity. The antimicrobial agent must act without adverse effects on human tissues, and must not impair tissue regeneration. Preferably, the antibacterial agent selected is devoid of offensive taste or odor. In general, the best known antibacterial agents include antibiotics such as the penicillins, beta-lactam antibiotics, tetracyclines, aminoglycosides, cephalosporins, macrolides, vancomycin, bacitracin, chloramphenicol and their salts. However, non-antibiotics may be desirable in addition to or in lieu of antibiotics, such as quinolones, sulfonamides and nitrofurans. For the purposes of this invention, the most preferred antibacterial agent is a penicillin. Another preferred antibacterial agent is a tetracycline.

The medicaments of this invention are chiefly composed of a pure, active crystalline powder of at least one antibacterial agent, thereby facilitating delivery of the highest possible concentration of the antimicrobial agent(s) to the site of the infection. The troche form of the invention is preferable over the powder, as it is easier to directly apply antibacterial agent in concentrated levels to an infection.

To initiate treatment via the preferred embodiments, a troche or small amount of powder containing at least one antibacterial agent (for instance, preferably between about 2–200 mg, and most preferably about 50 mg) may be mechanically placed in contact with the infected area of the oral mucosa. The troche or powder may be mechanically directed in place, for example, by the fingers. Once in contact with the infected area, the troche or powder may be held in position by the tongue, or by the pressure of the cheek, permitting the troche or powder to completely dissolve in saliva, ideally in about 5 to about 15 minutes. The direct release of the contents of the troche or powder to the mucosal infection creates an extraordinarily high (that is, a supratherapeutic) level of antibacterial agent concentration at the site of the infection. Thus, unlike previous liquid or tablet therapies for oral infections, which utilized moderate amounts of antibacterial agents intended to be swallowed at some point, the invention provides a unique approach to treating such infections, comprising a local oral treatment with a high concentration of dry therapeutic agents in troche or powder form.

By creating a supratherapeutically high level of antibacterial agent on the surface of the infected area, the extraordinarily high concentration gradient favors diffusion of the water-soluble antibacterial agent molecules through the ulcerated or damaged mucous membrane covering the infection into the deeper inflamed tissues to reach a concentration there that is substantially higher than the antibacterial agent levels that can be achieved via the blood stream by the conventional gastrointestinal absorption or by parenteral injections. In order to be effective, the dosage should be sufficient to achieve a concentration of at least 1 mg/ml, and preferably at least 2 mg/ml, of antibacterial agent in the human saliva. Preferably, the initial concentration is about 500 mg/ml and the trough concentration at the end of one hour is at least 2 mg/ml.

For instance, where the antibacterial agent is penicillin, the initial peak concentration of penicillin in saliva at the site of the infection may be about 800,000 Units per 1 ml saliva, and the local trough concentration of penicillin in saliva at the infection site may be about 7.5 mg (about 12,000 Units) per 1 ml saliva at the end of 1 hour. Where the antibacterial agent is oxytetracycline hydrochloride, the initial peak concentration of oxytetracycline hydrochloride in saliva at the infection site may be between about 400–800 mg per 1 ml saliva, and the local trough concentration of oxytetracycline hydrochloride in saliva at the infection site may be about 8 mg per 1 ml saliva at the end of 1 hour.

The only ingredient that must be present in the medicament is an appropriate antibacterial agent in dry form. However, it is preferred that the medicament contains an effective amount of one or more innocuous polyvalent metal compounds. Some polyvalent compounds are used in the pharmaceutical arts as lubricants for making oral tablets, as disclosed, for instance, in U.S. Pat. No. 5,534,262 to Dobrotvorsky et al. However, upon release from the invention, polyvalent metal compounds form a protective barrier at the site of mucosal ulceration. In addition to forming a physical barrier by which it protects the infected tissue, the polyvalent metal ion released from the polyvalent metal compound, especially the magnesium ions, also promotes the healing of the infected tissue by inducing the migration and phagocytic activity of various cell types integral in wound healing. For example, macrophages, fibroblasts and endothelial cells recruited by metal ions to the injured oral tissue phagocytize invading microbes, establish extracellular matrices, and promote neovascular formation. These known principles are disclosed in, for example, J. Clin. Invest. (1995), 95(1): 227–233 and Kitasato Arch. Exp. Med. (1991), 64(4):263–269, the contents of which are incorporated by reference herein in their entirety.

The polyvalent metal compound comprises a salt or an oxide of a member selected from the group of metals consisting of magnesium, zinc, calcium bismuth, aluminum, titanium and copper. Preferably, the polyvalent metal compound is a fatty acid salt of a metal, such as a stearate, citrate, benzoate, chloride or a sulfate, or other organic or inorganic acid salt. More preferably, the polyvalent metal compound is a fatty acid salt of magnesium or zinc. The metal compound may be an oxide, although the latter is generally more irritating to the normal oral mucosa than are fatty acid salts.

As mentioned above, the polyvalent metal compound is preferably delivered in a concentration sufficiently high that, when the troche or powder is dissolved in saliva at the site of infection, it forms a protective barrier over the site. This is best accomplished when the metal compound is delivered to the site in a concentration of between about 2–50 mg (preferably 10 mg) per 1 ml of saliva. To that end, it is preferred that the amount of polyvalent metal compound in the troche or powder is between about 0.2–5 mg. Most preferably the polyvalent metal compound is magnesium stearate, present in a range of about 0.5 to about 2.0 mg. Higher concentrations of magnesium stearate may be used, but such levels are prone to irritating the oral mucosa. The polyvalent metal compound, upon release from a troche or powder contacting an infected area, achieves a suspended concentration of about 10 mg/ml in saliva. Magnesium stearate and zinc stearate have been used in skin dusting powders, for they are not "wetted" by moisture, and permit seepage and evaporation. In the current invention, magnesium stearate is chosen as an agent to form a protective membrane on the surface of the site of the infection while permitting easy diffusion of antibacterial agents into the inflamed tissues.

In one preferred embodiment, the antibacterial agent is a penicillin and the polyvalent metal compound is magnesium stearate. In such a case, preferably the amount of penicillin in the troche or powder is about 50 mg and the amount of magnesium stearate is about 1.0 mg.

In another preferred embodiment, the antibacterial agent is a tetracycline and the polyvalent metal compound is magnesium stearate. Here, preferably the amount of tetracycline in the troche or powder is about 50 mg and the amount of magnesium stearate is about 1.0 mg.

Other compounds may also be included, such as inactive binding agents, which do not significantly interfere with the effectiveness or activity of the antibacterial agent (such as binding agents conventionally used in pharmaceutical formulations). Examples include polymeric binding agents, such as methyl cellulose, ethyl cellulose and hydroxycellulose. Other examples include synthetic polymers, such as polyvinylpyrrolidone, gums, starches, lactose, sucrose and other binding agents commonly known in the art.

The administration of the medicament depends upon the type of infection to be treated and the type and dosage of the antibacterial agent used. The appropriate antibacterial agent, dosage and treatment regimen can readily be determined by someone having ordinary skill in this art. In general, the invention is effective to treat most infections when properly administered four times daily after meals and prior to bedtime. Thorough tooth cleaning is advised prior to introduction of the medicament to an infected area. When the invention is applied properly as described, the painful sensation of most infections will markedly be reduced in 24 hours and becomes imperceptible in 48 hours, and complete healing will generally occur in about two to about four days.

To that end, it has been found that topical application in dry dosage form of 50 mg of penicillin G potassium or 50 mg tetracycline HCL or its equivalent, for example doxycycline hyclate (the three preferred antibacterial agents), four times a day (the preferred administration), resulted in complete relief of pains associated with minor aphthous ulcers, gingivitis and periodontal infections, within about 48 hours in over 90% of the patients. The inventor has further found that a tablet of 50 mg of penicillin G potassium, when dissolved in a loculated pocket of saliva brings about an initial local concentration of about 480 mg/ml penicillin G potassium at the site of the application, decreasing precipitously to about 7.5–15 mg/ml in one hour. Based on in vitro studies, a concentration of between 1–2 mg/ml of penicillin G potassium, tetracyclines or ciprofloxacin is sufficient to kill or to inhibit the growth of practically all bacteria in the saliva that can be cultured on blood agar plates. Therefore, medication with 50 mg of penicillin G potassium topically can sterilize a pocket of saliva bathing an infected area in the mucosa. This latter conclusion is further supported by results of in vivo studies. The inventor also found that the microbes in the exudate covering the raw surface of a canker sore or other mucosal infection are highly diverse in morphology, but are practically eliminated by the topical treatment with penicillin G potassium in 48 hours. In addition, four intermittent periodic medications of penicillin G potassium in the recommended manner of usage did not seem to alter the dominant microbial components of the normal flora in the human saliva.

It is also contemplated that this medicament and the methods of its administration may be used in conjunction with other medicaments and administrations (such as oral, parenteral, etc.) as part of a regime to treat or prevent an oral infection. For instance, a physician or dentist may desire to supplement a treatment of a complicated, deep-seated gingival bacterial infection, using a combination of a systemic administration of antibiotics and a topical medication as described herein.

The invention will become more apparent in the following non-limiting examples.

EXAMPLES

Example I

TABLE 1

Production and Use of Penicillin/Magnesium Stearate Troches

| Compound | |
|---|---|
| Penicillin G or penicillin V potassium salt | 50.0 mg (80,000 Units) |
| Magnesium stearate | 1.0 mg |
| Stearic acid | 0.6 mg |
| Lactose | 7.5 mg |
| Polyvinylpyrrolidone, cellulose esters and starch binding agents | Balance |
| Total weight | 73.0 mg |
| pH in ddH20 | 6.8–7.2 |

Table 1 shows the reagents combined to make penicillin/magnesium stearate troches. The reagents were mixed in the listed proportion in powder form, with an adequate amount of moisture added to permit standard pharmaceutical compression of the composition into troches weighing about 73 mg. Sample troches selected at random were crushed and suspended in 2 ml of double-distilled water, yielding a neutral acidity of pH 6.8–7.2. Upon placement in a stationary location of the human oral cavity, each therapeutic troche should completely disintegrate in saliva within about 10 to about 15 minutes without causing desquamative injuries or erosion to the intact oral mucosa.

It is noted that this example is equally applicable for the treatment of acute gingivitis and for aphthous stomatitis. Complete relief of painful sensation is generally achieved in 48 hours. However, there is no grossly visible breakdown of mucous membranes in acute gingivitis. The endpoint of healing in the latter condition is not as easy to evaluate objectively as in aphthous ulcers.

Patients with aphthous ulcers were advised to brush their teeth to rid them of food residues, and to rinse their mouths with water prior to initiating treatment. One penicillin/magnesium stearate troche was placed in the patients mouths directly over the ulcerated lesion. The troche was dissolved or disintegrated in a minimum amount of saliva directly over the ulcer in no more than 15 minutes, preferably in about 8 to about 12 minutes. The patients were advised to keep the ingredients of the disintegrated troche at the site of the lesion as long as possible. Food and beverages were avoided for one hour after each treatment. If multiple aphthous ulcers were present, only one troche is required for the treatment of a cluster of small ulcers. The topical treatments were conducted 4 times daily, for example, after breakfast, after lunch, after dinner and before bed time for no more than 4 days. During the first application, some patients felt a slight burning sensation over the ulcer, as the raw ulcers were not protected from irritation. The burning sensation lessened with subsequent applications. The painful symptoms markedly improved after 24 hours, and became largely imperceptible in 48 hours. Treated ulcers displayed visible signs of healing within 2 days, and complete healing within 4 days.

For instance, the first sign of healing is usually the fading of the hyperemic zone at the periphery of the ulcer and the lessening of edema at the base of the ulcer. The membrane covering the ulcer becomes thinner, more translucent, more pearly white instead of a grayish-yellowish white prior to the application and contract with the troche. This process of healing can be observed within 24–48 hours after the first medication, and continues until the whitish membrane sloughs off completely and replaced by the newly regenerating mucosa directly underneath. The size of the ulcer reduces simultaneously.

But the major healing process takes place underneath the membrane at the base of the ulcer. After 4 days of penicillin medication, usually only remnants of a thin pearly whitish membrane remain, if any, covering an incompletely re-epithelialized newly healed ulcer. Also, there was no observed adverse reactions of stomatitis or discoloration of the tongue.

Bacterial counts in the saliva taken from the oral cavity of five patients in the vicinity of the ulcer were conducted. Saliva samples of 10 microliters were pipetted immediately before and 24 hours instituting penicillin troche medication, and each sample as spread on the surface of a 10-cm blood agar Petri dish. The inoculated plates were incubated anaerobically at 37° C. and observed at 18 and 42 hours. The plates inoculated with samples taken before treatment always showed numerous bacterial colonies, ranging from 50 to more than 300 in number, including Neisseriae, Bacteroides, Fusibacteria, *Streptococcus viradans*, Diphtheroids, Non-group A Streptococci, *Proteus mirabilis*, and *Staphylococcus aureas*. After 24 hours of penicillin medication, no bacterial colonies, except occasional yeast-form fungal colonies, were observed after incubation, indicating a total inhibition of the opportunistic pathogenic bacteria in the saliva of the patients under the medication of supratherapeutic dosage of penicillin.

Application of the penicillin/magnesium stearate troches in the aforementioned manner created a supratherapeutic concentration of penicillin on the raw surface of the apthhous ulcer. Assuming that the troche is dissolved in 0.1 ml of saliva locally at the ulcer, the initial concentration of penicillin would reach up to 500 mg/ml, and that of magnesium stearate 10 mg/ml. Under the influence of this extraordinarily high concentration of penicillin G or penicillin V, most microorganisms of the normal flora cannot survive or continue to multiply, permitting tissue regeneration processes to occur under the protective barrier coating formed by the magnesium stearate.

The local concentration of penicillin in the saliva was determined as follows. One troche containing 50 mg of penicillin G was placed in the sulcus between the lower gum and the buccal mucosa of the patient to be dissolved in a minimum amount of saliva. This loculated pocket of saliva was not swallowed and was not to be diluted with excess saliva from other parts of the mouth for one hour. Two samples were taken for assay to determine the peak and trough local concentrations of penicillin during the one-hour duration of medicinal treatment. At the time when the troche was completely dissolved and one hour later, aliquots of 10 microliters were pipetted from this pocket of saliva solution at the site of medication, representing the peak level and the trough level of antibiotic concentration, and transferred into 10 ml of distilled water to make a 1:1.000 dilution and into 1 ml of distilled water to make a 1:100 dilution, respectively. The diluted saliva antibiotic solutions were passed through a sterile bacteria-filter to remove any bacterial or fungal contaminants of the oral flora.

For determination of the peak concentration, 1 ml of the bacteria-free filtrate was further diluted with 9 ml of nutrient broth to achieve a 1:10,000 dilution of the saliva. Then a serial two-fold dilution was made of this 1:10,000 diluted saliva sample with an equal volume of nutrient broth in a roll of test tubes to obtain a series of 1 ml aliquots of nutrient broth in which the saliva was diluted to 20,000, 40,000, 80,000, 160,000, 320,000, 640,000, 1,280,000 and 2,560,000 folds respectively. One ml of nutrient broth which had been freshly inoculated with a young culture of a standard strain of *Staphylococcus aureus* (ATCC 29213) having a known minimum inhibitory concentration (MIC) at the range of 0.25–2 units of penicillin/mi was added to each test tube. Thus the final dilutions of the saliva sample were in the range of 40,000 to 5,120,000 folds.

For determining the trough concentration, the entire 1 ml of the 1:100 diluted saliva filtrate was used to make the serial dilutions so that the final dilutions of saliva sample were in the range of 4,000 to 256,000 folds in the final test culture.

As control standards, a series of test tubes containing 1 ml of nutrient broth with varying concentrations of penicillin G potassium salt ranging from 0.1 units to 10 units/ml were similarly mixed with an equal volume of nutrient broth freshly inoculated with the standard tubes of Staphylococcus aureus. Both the test and control standard tubes were incubated at 37° C. for 18 hours. Among the test tubes showing no gross evidence of bacterial growth, the one containing the highest dilution of saliva and the one containing the least amount of penicillin G were considered as having the identical concentration of penicillin, i.e. the MIC of the staphylococcus aureus.

In three experiments conducted as described above, the MIC of penicillin G for the standard strain of *Staphylococcus aureus* (ATCC 29213) was found consistently to be at 1 unit/ml. The maximum final dilutions of the saliva in nutrient broth in which the bacteria failed to show growth were found to be 1/640,000, 1/1,280,000 and 1/640,000 or the peak concentration samples, and to be 1/4,000, 1/16,000 and 1/64,000 for the rough concentration, respectively. Therefore, it was concluded that the initial peak local concentration of penicillin, although the antibiotic might not be in a strict solution formn, had reached 640,000–1,280,000 units/ml in the saliva at the site of topical medication when the troche was allowed to dissolve in a loculated pocket of saliva directly over the canker sore, or about 800,000 units/ml, equivalent to 500 mg/ml of penicillin G. Since a troche contains 50 mg of penicillin, it may be deduced that the troche was dissolved in about 0.1 ml of saliva at the time of its complete dissolution. After application of 50 mg of penicillin G potassium in dry dosage form, at the end of the one-hour medicinal treatment duration the concentration of penicillin was markedly reduced to a low level of 7.5–15 mg/ml.

In comparison, after a single dose of intravenous injection of penicillin G, usually 500 mg in medical practice as reported in the literature, the average peak blood level is about 16 mcg/ml, or about 26 units/mi. Injecting higher doses may be hazardous and will not increase the blood or the tissue levels because of rapid clearance by the kidneys. Therefore, it is theoretically impossible to deliver a penicillin to the oral mucosa at a concentration of even 100 units/ml via the standard forms of medication through gastrointestinal absorption, intramuscular injection or intravenous injection.

Thus, it is concluded that administering a 50 mg penicillin troche as described in this invention as a topical medication for the treatment of canker sores can produce at the site of the lesion a local peak concentration of penicillins of about 800,000 units/ml, or 500 mg/ml, and a local trough concentration of about 7.5–15 mg/ml. This level of antibiotic concentration which can be maintained for at least one hour is about 470 to 30,000 times the highest blood level that can be achieved by the conventional routes of medication via gastrointestinal absorption, or intramuscular or intravenous injections.

Example II

TABLE 2

Production and Use of Oxytetracycline Hydrochloride/Magnesium Stearate Troches

| Compound | |
|---|---|
| Oxytetracycline hydrochloride | 50.0 mg |
| Magnesium stearate | 1.0 mg |
| Stearic acid | 0.6 mg |
| Lactose | 7.5 mg |
| Polyvinylpyrrolidone, cellulose, esters and starch binding agents | Balance |
| Total weight | 73.0 mg |
| pH in ddH20 | 6.8–7.2 |

Table 2 shows the reagents used to synthesize oxytetracycline/magnesium stearate troches. The oxytetracycline hydrochloride troches were prepared as described in Example 1. These troches were designed for patients with allergies to penicillins.

Canker sores are used as an example for demonstration of the effectiveness of the treatment for acute bacterial infections of the oral mucosa-stomatitis. The treatment is equally effective for acute gingivitis with painful sensation completely relieved in 48 hours.

When the oxytetracycline hydrochloride/magnesium stearate troches are applied in the manner described in Example 1, extraordinarily high concentrations of antibiotic were released on the raw surface of the treated ulcers. Assuming that the troche is dissolved in 0.1 ml of saliva, the peak concentration of oxytetracycline would be between about 400–800 mg/ml locally at the site of the ulcer, and that of magnesium stearate 10 mg/ml.

A similar experiment to the one described in Example I was designed and conducted in two subjects to test the initial peak concentration and the one-hour trough concentration of oxytetracycline hydrochloride in the loculated pocket of saliva after a troche containing 50 mg of the antibiotic was grossly dissolved in the sulcus between the lower gum and the buccal mucosa. The final concentrations of oxytetracycline in the control standard nutrient broth were 0.25 mcg/ml, 0.5 mcg/ml, 1.0 mcg/ml, 2.0 mcg/ml, 4.0 mcg/ml, and 8.0 mcg/ml. The final dilutions of saliva sample were 1/50,000, 1/100,000, 1/200,000, 1/400,000, 1/800,000 and 1/1,600,000 for the peak concentration test tubes and 1/4,000. 1/8,000, 1/16,000 and 1/32,000 for the trough concentration test tubes. The *Staphylococcus aureus* (ATCC 29213) was also used as the standard test microorganism. The results showed that this organism exhibited a sensitivity to oxytetracycline hydrochloride at an MIC of 1 mcg/ml. According to the methodology outlined above, the initial peak concentrations of oxytetracycline hydrochloride in saliva were calculated to be 400 mg/ml and 800 mg/ml, and trough concentrations to be 8 mg/ml and 8 mg/ml in these two experiments.

In the medical literature, it has been reported that after intravenous drips of 200 mg of tetracyclines, the average peak blood level usually reaches 4 mcg/ml. Intravenous injections of larger doses of tetracyclines are not recommended because of undesirable side-effects and complications. When the antibiotic troche of this invention is made of 50 mg of oxytetracycline hydrochloride, which cannot be safely injected in a single large dose, the advantage is remarkable. The trough and peak concentrations are about 2,000 to 100,000 times the peak blood level usually quoted in the medical literature. The inventor believes that this supratherapeutic level of antibiotics delivered directly over the lesion is one of the reasons for the success in using this dry dosage form of medication to treat canker sores.

Example III

TABLE 3

Production and Use of Penicillin/Magnesium Stearate Powder

| Compound | |
|---|---|
| Penicillin G or penicillin V potassium Salt | 5000 mg (80,000 Units) |
| Magnesium stearate | 80 mg |
| Stearic acid | 60 mg |
| Lactose | 750 mg |
| Starch | 110 mg |
| Total weight | 6000 mg |

Table 3 shows the ingredients combined to make the penicillin/magnesium stearate powder of this invention. The above ingredients are in fine powder and mixed. An aliquot of 60 mg of the powder suspended in 2 ml of double-distilled water should yield a neutral acidity of pH 7.0+/−0.2, and should not cause desquamative injuries or erosion when applied to a localized spot of about 5 mm in diameter on an intact oral mucosa.

This formula is generally useful for children who may not be able to use the penicillin troches according to the directions given in Example I. Instead, an applicator (such as, for instance, a small easily opened packet) or an adult's finger will be used to apply the medicinal powder in the amount of 30 to 60 mg directly to the canker ulcer four times a day after meals and drinking. Acute gingivitis is equally effectively treated.

If there are multiple canker ulcers in the mouth and are located far apart from one another, only one dose of powder is required for the treatment of a cluster of ulcers. The patient is not given any food or drink for one hour. If the ulcer does not show any sign of healing in four days, the physician should pursue further investigation for diseases other than canker ulcers.

Example IV
Concentrations of penicillin G demonstrating inhibition of bacterial growth in human saliva in vitro For this study, five healthy adult volunteers, three men and two women, were asked to refrain from drinking and eating for two hours after breakfast. At the end of two hours, about five (5) ml of saliva was obtained from the oral cavity of each volunteer. Aliquots of 0.1 ml of saliva were pipetted immediately from each saliva sample and spread over the surface of two 5% sheep blood agar plates with a sterile plastic loop. One inoculated blood agar plate was incubated in an aerobic atmosphere containing 5% CO2, and the other anaerobically at 37° C. for 18 hours, as untreated controls.

Aliquots of 0.2 ml of the saliva from each volunteer's sample were pipetted into sterile test tubes, and labeled from No. 2 to No. 13. Five equal doses of dry powder of the USP grade penicillin G potassium salt, 200 mg each, were weighed and put into five sterile test tubes, all labeled No. 1. The dry powder of antibiotic was dissolved in 0.4 ml saliva obtained from each of the five volunteers to constitute an initial concentration of antibiotic concentration of 500 mg/ml in saliva. An aliquot of 0.2 ml of the saliva antibiotic solution was pipetted from tube No. 1 into tube No. 2. After having been thoroughly mixed, 0.2 ml of the content in tube No. 2 was pipetted to tube No. 3, and so forth continuously in succession to make a serial double dilution of penicillin G potassium solutions in saliva through tube No. 13. Finally, the test tubes contained different concentrations of penicillin G potassium in the saliva of five volunteers, as follows.

TABLE 4

| Tube No. | Concentration of penicillin G potassium (mg/ml saliva) |
| --- | --- |
| 1 | 500 |
| 2 | 250 |
| 3 | 125 |
| 4 | 62.5 |
| 5 | 31.25 |
| 6 | 16 |
| 7 | 8 |
| 8 | 4 |
| 9 | 2 |
| 10 | 1 |
| 11 | 0.5 |
| 12 | 0.25 |
| 13 | 0.125 |

The mixtures of antibiotic and saliva in the test tubes were incubated at 37° C. One hour later, an aliquot of 0.1 ml was pipetted from the content of each tube, first dropped in the center of a blood agar plate and then spread to the periphery of the plate surface. The plates were incubated aerobically at 37° C. with 5% carbon dioxide in the atmosphere for 18 hours and were examined for bacterial growth.

Figure 2:
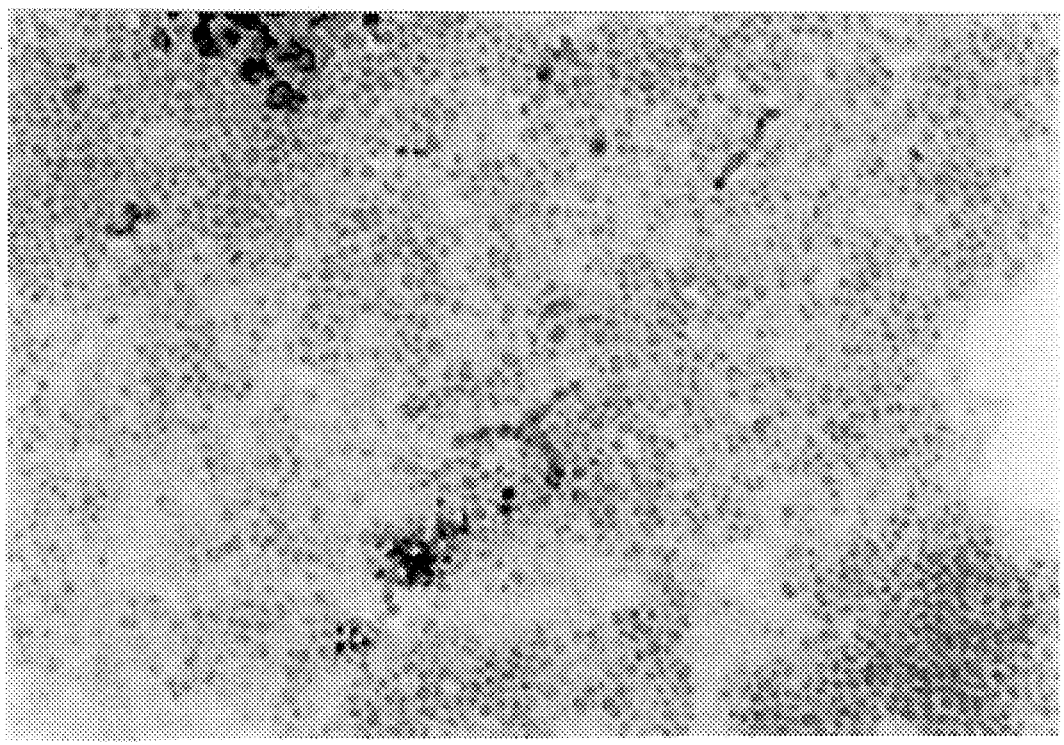
FIG. 2 Gram-stain of the culture on plate of FIG. 1, showing mostly Gram-negative diplococci and a few short chains of Gram-positive cocci.
Figure 3:
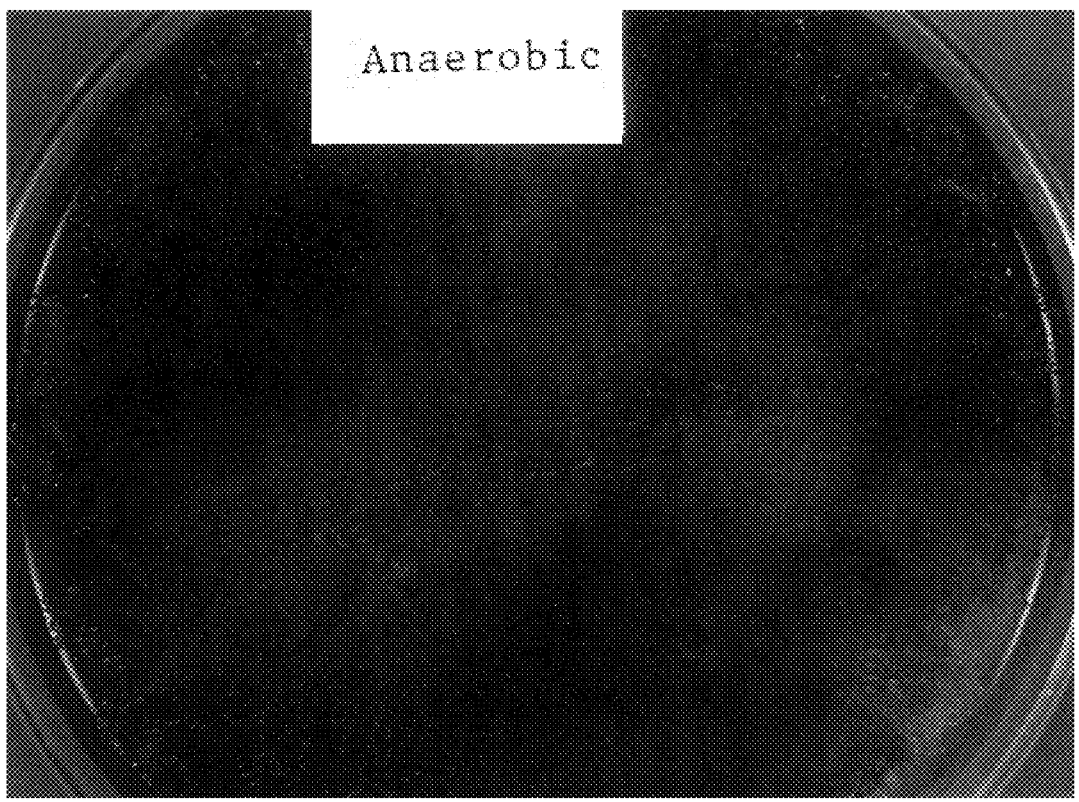
Figure 4:
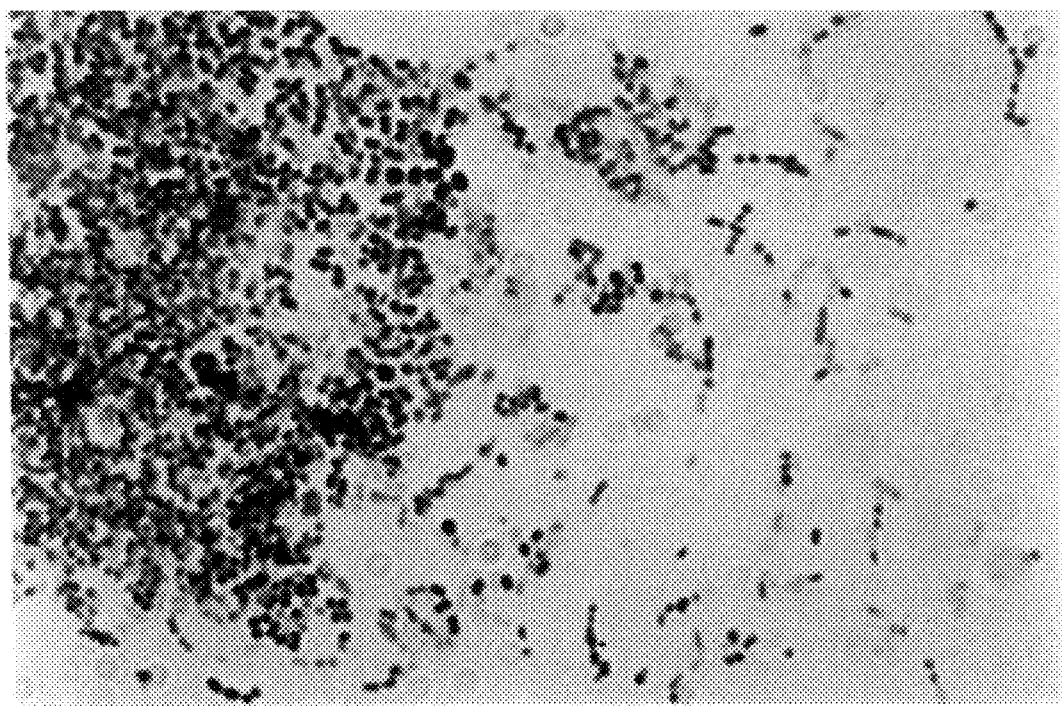

The blood agar plates inoculated with 0.1 ml of saliva samples without antibiotic treatment all showed numerous bacterial colonies on the surface of the plate, the number being too numerous to count and estimated to exceed 3,000 colonies per plate inoculated with 0.1 ml of saliva. The majority of the colonies were those of Neisseriae and non-β-hemolytic streptococci, especially *Streptococcus viridans*. When the plates were incubated aerobically, the growth was dominated by Neisseriae (FIGS. 1 and 2). When the plates were incubated anaerobically, the majority of the colonies were non-β-hemolytic streptococci (FIGS. 3 and 4), mostly *Streptococcus viridans*. No efforts were made to identify the individual species, to recover the minority colonies or colonies which grew well only under anaerobic conditions. However, when small loops of the saliva samples were streaked on blood agar plates for culture, occasional colonies of diphtheroids, lactobacilli, bacteroides, spore-forming bacilli and actinomyces were observed. These were considered to be normal minority inhabitants in the human saliva.

Figure 5:
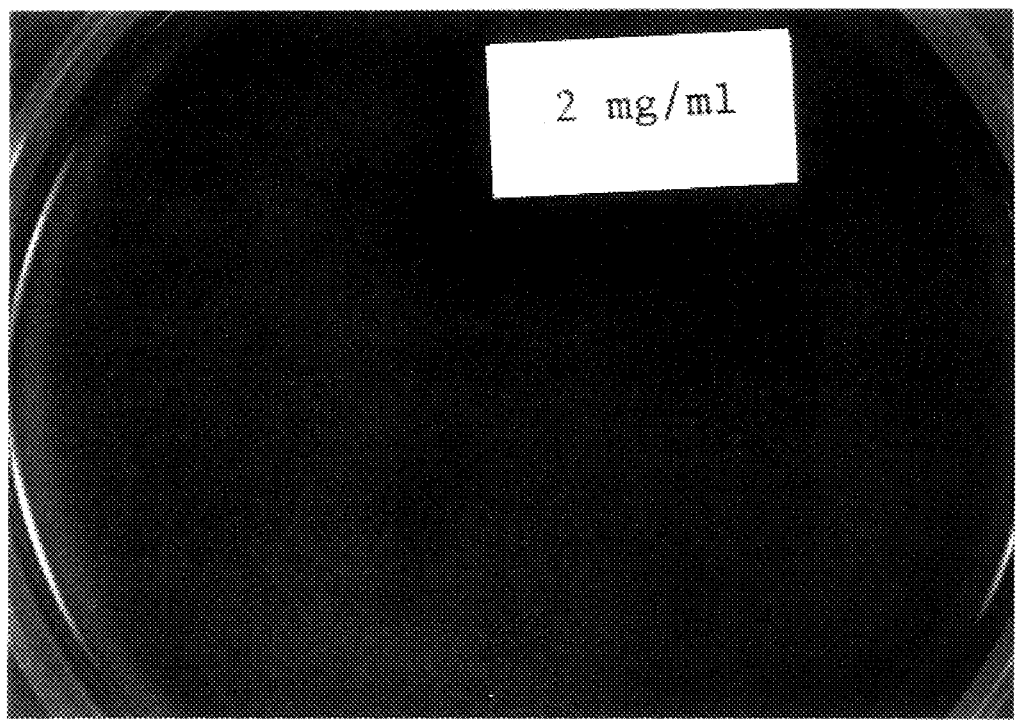
FIG. 5 All bacteria in the saliva were either destroyed or totally inhibited by penicillin G potassium at a concentration of 2 mg/ml or above.
Figure 6:
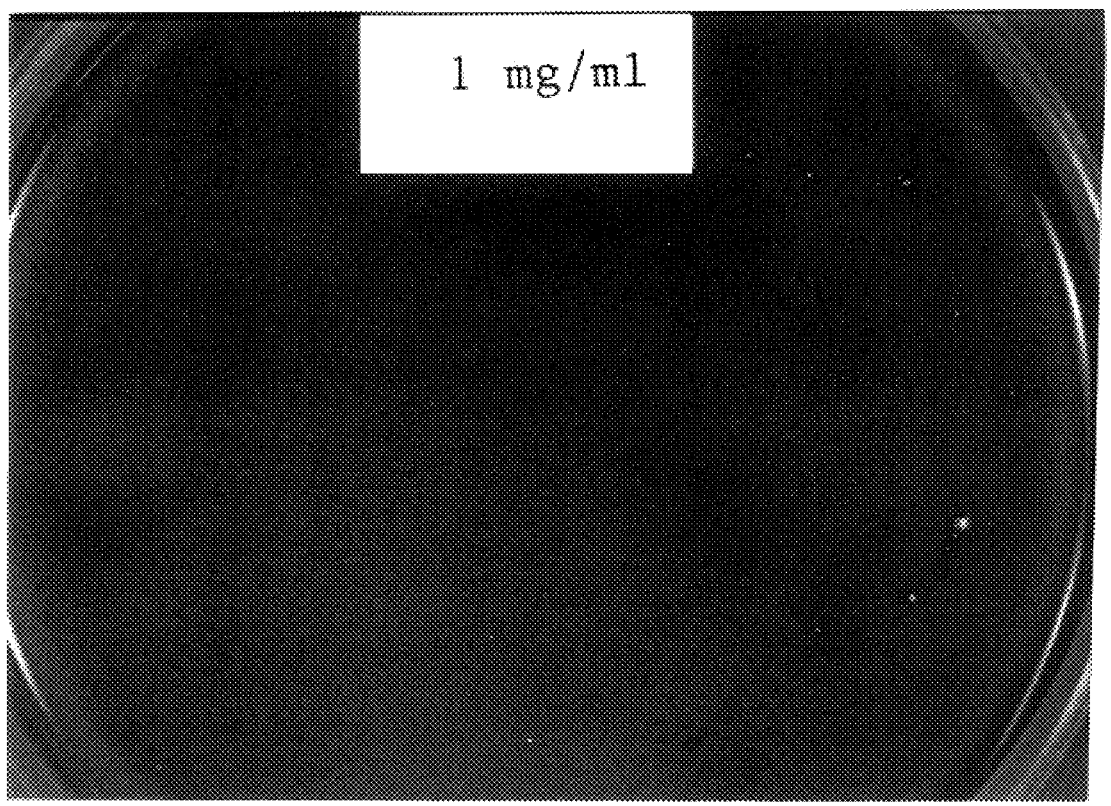
FIG. 6 A few surviving or uninhibited bacteria grew into colonies at the periphery of the salivary inoculum where the penicillin G potassium concentration dropped down to 1 mg/ml in the saliva.
Figure 7:
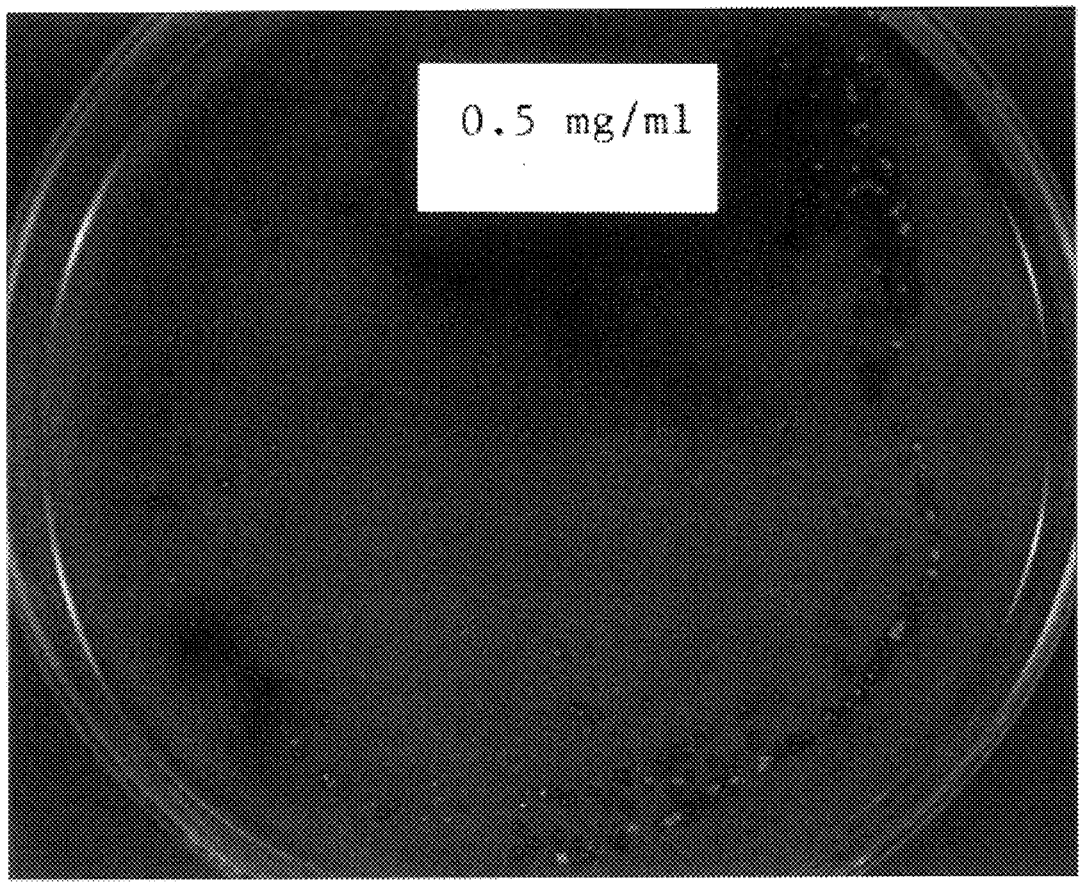
FIGS. 7 & 8 Progressively more surviving or uninhibited bacteria grew into colonies at the periphery of the salivary inoculum where the penicillin G potassium concentration dropped down to 0.5 mg/ml, 0.25 mg/ml and lower.
Figure 8:
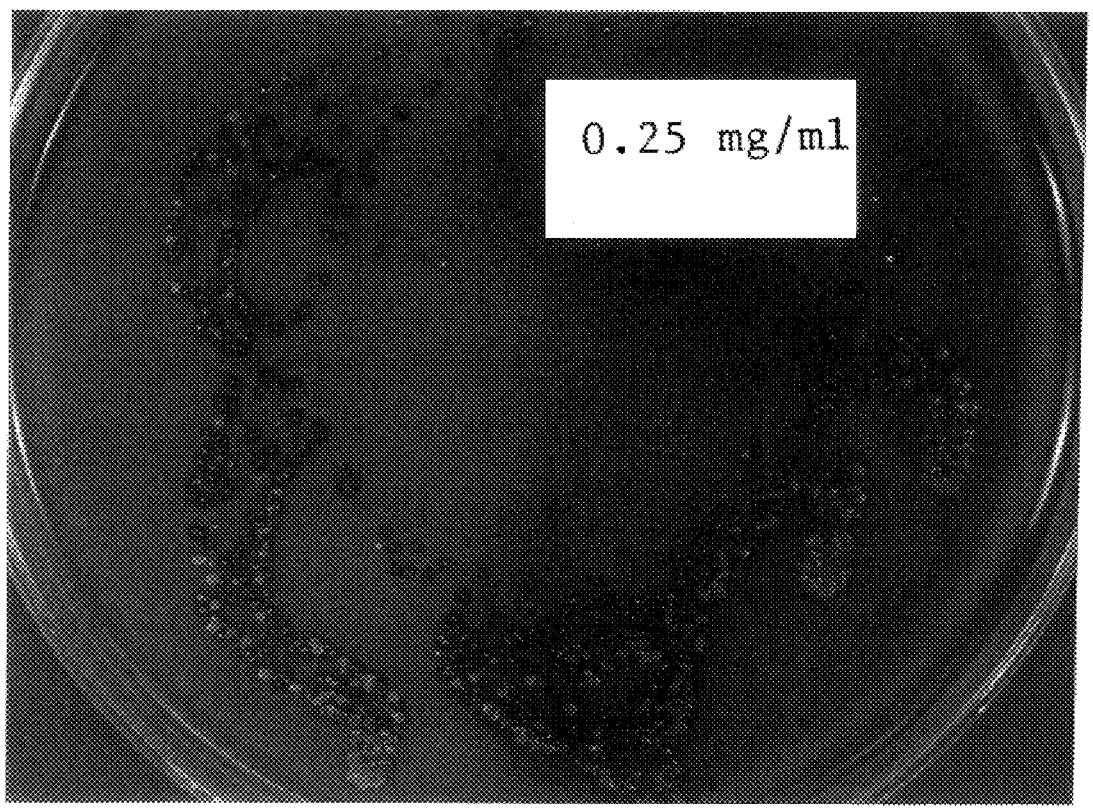

No bacterial colonies were visible on the blood agar plates inoculated with contents from tubes No. 1 to No. 9 for all five normal volunteer saliva samples. This finding was reproduced in all five samples and indicates that a concentration of penicillin G potassium at 2 mg/ml (FIG. 5) or higher inhibits the growth of all bacteria in the human saliva that can grow aerobically on blood agar. Scattered bacterial colonies began to appear as the concentration of penicillin G potassium decreased to about 1 mg/ml (FIG. 6). The number of bacterial colonies progressively increased as the concentration of antibiotic in the saliva was reduced (FIGS. 7 and 8). On each plate showing partial bacterial growth, the colonies at the periphery of the plate invariably grew bigger in size and more numerous in number. This result indicates that at certain "marginal" concentrations (for example at 1 mg/ml, which is equivalent to 50% of an MIC level) penicillin G was not "bactericidal" within one hour's incubation time. After being transferred to a blood agar plate, the surviving bacteria in the antibiotic-saliva mixture were able to resume multiplication at the periphery of the inoculum as the penicillin at that location diffused into the agar and thus lowered its local concentration to below their MIC levels in the immediate surroundings of the bacteria.

Based on the results of this study, it is concluded that a concentration of penicillin G potassium at or above 2 mg/ml practically inhibits the growth of all of the salivary bacteria which can grow aerobically. However, at 1 mg/ml or concentrations below this level the inhibition is not complete. In comparison to other broad-spectrum antibacterial agents, such as tetracyclines and quinolones (e.g., ciprofloxacin) which usually inhibit the growth of the oral flora in saliva at a concentration of 1 mg/ml (see below), a slightly higher MIC (2 mg/ml instead of 1 mg/ml) is found for penicillin G. This is because penicillin G is a labile antibiotic, subject to breakdown by various enzymes in the oral cavity, including the β-lactamases produced by the bacteria in the saliva.

The anaerobic microbes in the saliva were not measured because these organisms are believed not pathogenic on the surface of the oral mucosa without the co-operation of the aerobic or facultative anaerobic bacteria whose growth would reduce the oxygen tension, paving the way for the anaerobes to grow in the ulcerated lesions.

Example V
Inhibition of bacterial growth in the saliva in vivo by penicillin G potassium Five healthy adult volunteers, three men and two women, were asked to refrain from drinking or eating for two hours after breakfast. At the end of two hours, an aliquot of 0.1 ml of saliva was pipetted from the mouth of each volunteer and spread over the surface of a sheep blood agar plate with a sterile plastic loop. The inoculated blood agar plate was incubated in an aerobic atmosphere containing 5% CO2 as pre-medication control. Then 100 mg, 50 mg, 20 mg, 10 mg and 2 mg of penicillin G potassium dry powder, USP grade, were placed in the right buccal pouch with a spatula between the cheek and the lower gum of each volunteer, respectively.

The volunteers were asked to retain the dissolved penicillin powder at the site of medication as concentrated as possible, not to be diluted by saliva from other parts of the mouth for one hour.

At the end of one hour, 0.1 ml of saliva from each volunteer was pipetted from the right buccal pouch where the medication was placed, and inoculated and spread onto the surface of a sheep blood agar plate. The inoculum was spread with a sterile plastic loop. All plates so inoculated were incubated in an aerobic atmosphere containing 5% $CO_2$ at 37° C. for 18 hours, and the inhibition of bacterial growth by different doses of penicillin G potassium in saliva in the human mouth was observed and compared with the positive pre-medication control plates.

The results showed that there were no bacterial colonies on the blood agar plates inoculated with 0.1 ml of saliva sample taken from the human buccal pouches which were treated for one hour with a topical medication of 100 mg, 50 mg, 20 mg, or 10 mg of penicillin G potassium powder. The pre-medication control plates inoculated with 0.1 ml of saliva from these volunteers all showed numerous (more than 3,000) bacterial colonies, primarily of Neisseriae and non-β-hemolytic streptococcal species similar to those observed in FIGS. 1 and 2. On the blood agar plates inoculated with 0.1 ml of saliva sample taken from the human buccal pouch treated with 2 mg of penicillin G potassium powder, there were a few isolated bacterial colonies of Neisseriae and non-β-hemolytic streptococci, similar to those shown in FIGS. 6–8 observed with the in vitro study. Almost identical results were obtained in five separate studies.

The conclusion of this study is that at least 10 mg of penicillin G potassium powder is required to bring about a total cessation of bacterial growth in a small pocket of saliva in the human mouth. This effect can be achieved at least under ideal study conditions with co-operative volunteers who are able to follow instructions of directing proper saliva flows in the mouth during the one-hour long medication time. A smaller dose, for example, 2 mg of penicillin G potassium powder can only produce a partial inhibition of growth at the end of the first hour after medication. Throughout these study examples, it has been demonstrated that dry-dosage form of an antibacterial agent when used as topical medicaments as directed is initially dissolved in about 0.1 ml of saliva at the site of mucosal infection. In theory, as little as 0.2 mg of penicillin G would be sufficient to achieve an initial topical MIC concentration of 2 mg/ml. However, in practice, because of the continuous dilution effect of the saliva and the enzymatic breakdowns of penicillin G in the mouth, a higher dose of the dry active medicine is suggested to ensure the therapeutic MIC at the site of the infection.

Example VI
Bacterial inhibition in the saliva and in canker sore in vivo by penicillin G potassium Six (6) adult, otherwise healthy patients suffering from recurrent minor canker sores were selected for this study from July 10 to Nov. 12, 1998. The drug substance used for this study was crystalline penicillin G potassium salt, U.S.P. grade, purchased from Sigma Chemical Co., St. Louis, Mo. 63178 (Lot No. 57H1195). All the patients who participated in this study had a history of recurrent minor canker sores and were known to be not allergic to penicillins or other β-lactam antibiotics.

On the first or the second day after the patients noticed the formation of the canker ulcers, 50 mg of penicillin G potassium was administered topically with a spatula or the handle of a teaspoon as dry powder directly over the canker ulcers, four times a day, i.e. after breakfast, after lunch, after supper and before bed time. The patients were advised to retain the antibiotic powder and its concentrated solution in a small pocket of saliva at the site of the ulcer and to avoid its excessive dilution by saliva from other parts of the oral cavity for one hour after each application of the antibiotic powder. No food or drink was allowed during this one-hour period.

Before the initiation of treatment, a small amount of exudate was scraped off the grayish-white covering of the ulcer with a toothpick and mixed with a drop of aqueous solution of Congo red for a negative stain smear. After the dried smear was exposed to concentrated hydrochloric acid vapor, the negative-stained microorganisms were examined microscopically.

Samples of 0.1 ml of saliva at the site in the vicinity of the canker ulcer were pipetted from the mouth immediately before instituting the first penicillin G potassium application and about 60–70 minutes after the first antibiotic application. Each sample was spread on the surface of a 10-cm blood agar Petri dish with a sterile plastic loop. The inoculated plates were incubated aerobically at 37° C. for 18 hours as described above. The total numbers of bacterial colonies on each plate were estimated. The dominating species of the microorganisms were identified according to the approved protocols routinely used in a clinical microbiology laboratory. The results are tabulated as follows

TABLE 5

| Patient No. | Colonies Before Treatment | Colonies after Treatment |
|---|---|---|
| 1 | >3,000 N, S | 0 |
| 2 | >3,000 N, S | 2, Y |
| 3 | >3,000 N, S | 0 |
| 4 | >3,000 N, S | 0 |
| 5 | >3,000 N, S | 0 |
| 6 | >3,000 N, S | 0 |

Figure 9:
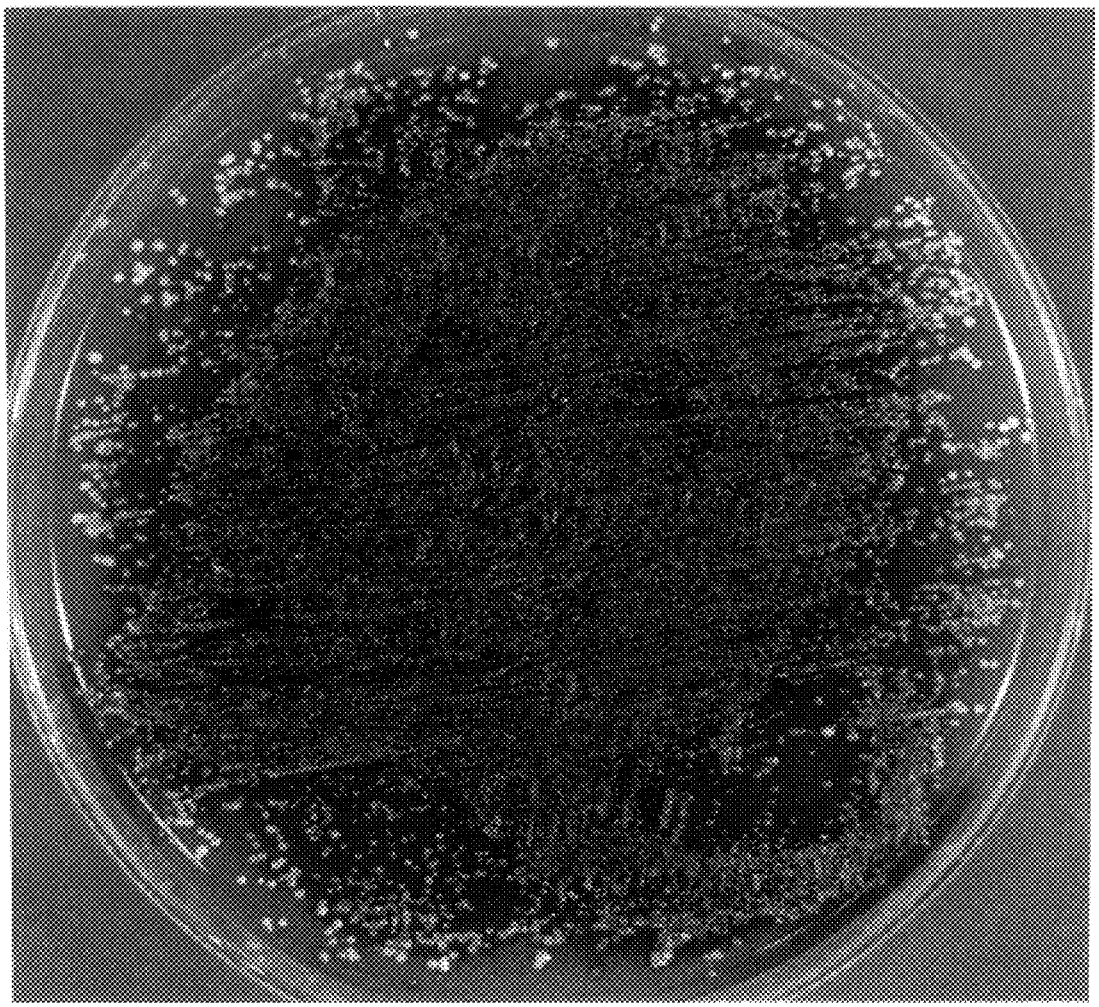
FIG. 9 Bacterial colonies in 0.1 ml of saliva taken from the mouth of a patient in the vicinity of a canker ulcer. Inoculated on the surface of a 5% sheep blood agar plate and incubated aerobically in an atmosphere containing 5% carbon dioxide at 37° C. for 18 hours. The culture is dominated by colonies of Neisseriae with those of non-β-hemolytic streptococci scattered in-between, similar to those demonstrated in FIG. 1.

The plates inoculated with saliva samples taken from canker sore patients before treatment always showed numerous bacterial colonies, over 3,000 per 0.1 ml (FIG. 9). The overwhelming majority of the colonies were those of Neisseriae (N) and non-β-hemolytic streptococci (S), as observed on the plates inoculated with saliva of normal volunteers. No attempts were made to identify all individual bacterial colonies observed or the minority members of the oral flora in individual patients since our preliminary bacteriologic studies and the studies published by other investigators have not demonstrated a specific pathogen for canker sores.

Figure 10:
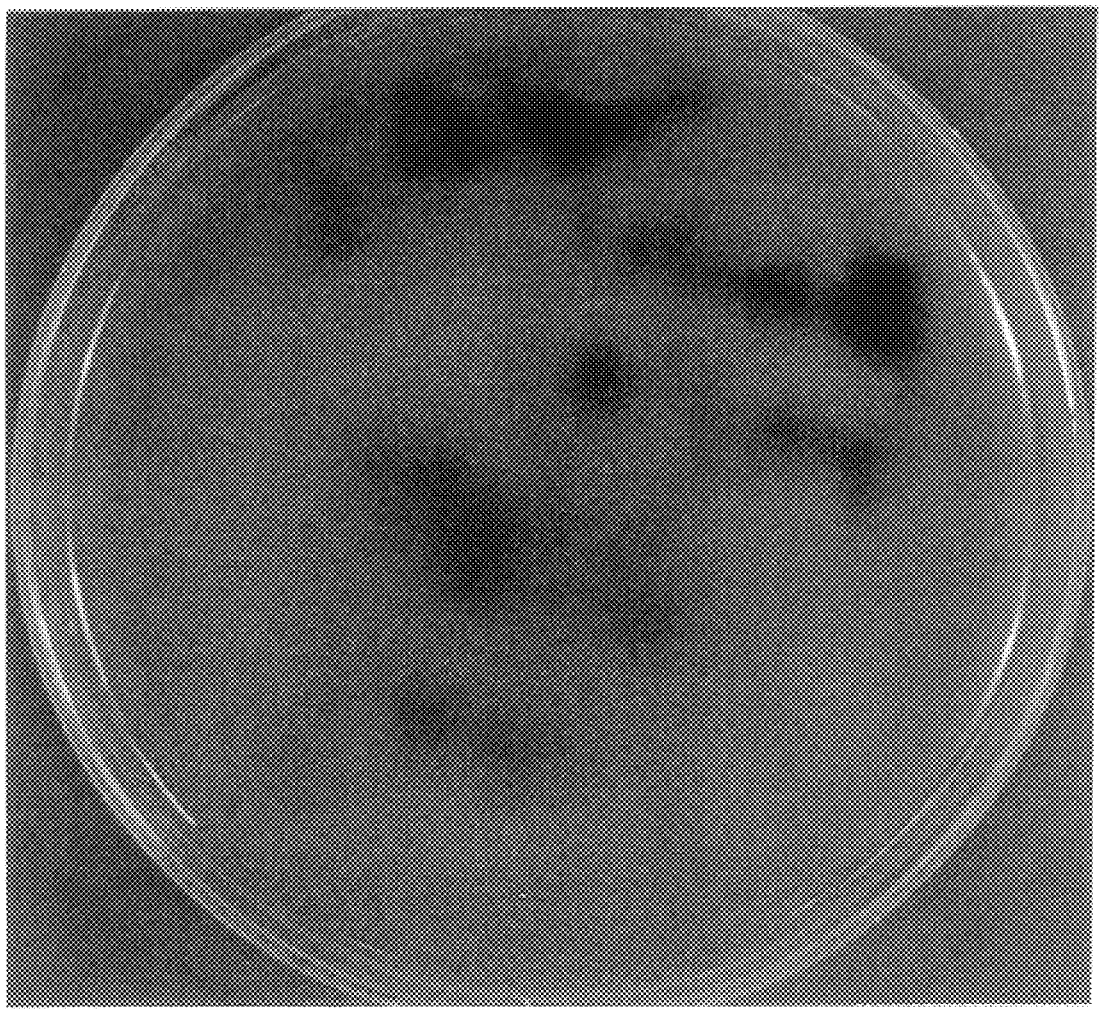
FIG. 10 Total inhibition of bacterial growth in the saliva taken directly from the mouth of a patient near a canker sore which was treated with a topical medication of 50 mg of penicillin G potassium dry powder.

After topical medication of 50 mg of penicillin G potassium for about one hour, the bacteria in the saliva covering the ulcer were totally destroyed or inhibited (FIG. 10). Two yeast-form colonies were observed in the saliva of patient No. 2 after penicillin treatment. These two colonies were identified as common yeast, *Saccharomyces cerevisiae* (Y).

Figure 11:
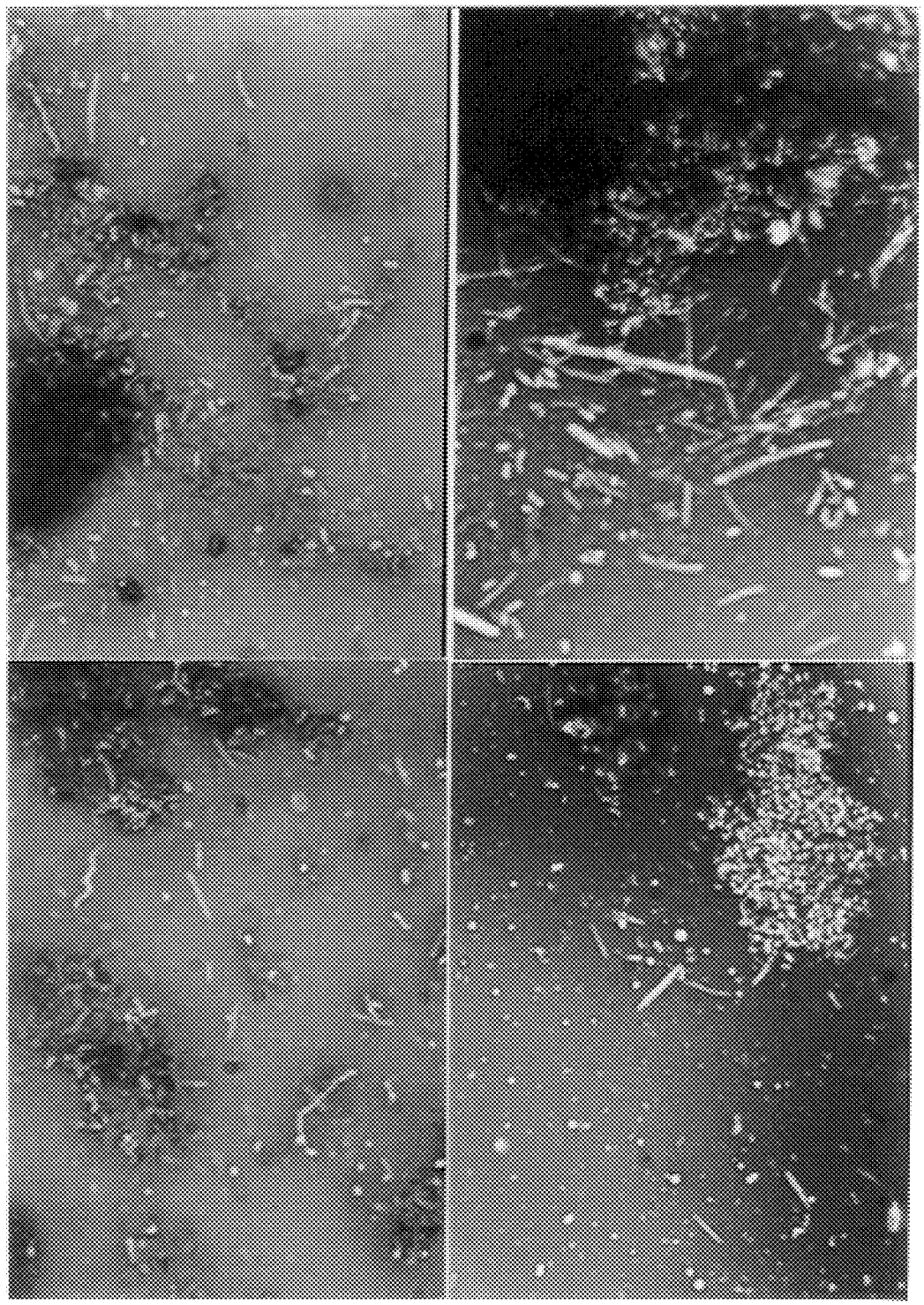
FIG. 11 Congo red negative stain of the exudate covering a canker ulcer. Selective fields microphotographed showing mixture of a variety of microorganisms, ranging from rods, cocci, and fusiform bacilli to spirochetes.

The Congo red negative stain of the exudate obtained before treatment showed a variety of microbes in the exudate covering the surface of the canker ulcer. These microbes include rods of different sizes, cocci, fusiform bacilli and spirochetes of variable sizes (FIG. 11), a consortium of microorganisms not reflected by the colonies observed on the blood agar plates. Many of these microorganisms were difficult to demonstrate with Gram-stain. It is well-known that only 20–30% of the microbial species living in the human oral cavity can be cultured by any one type of artificial media.

On day 2, about 48 hours after the medication was initiated, the patients collected an early morning sample of saliva immediately after getting up and submitted it to the laboratory for culture. While in the laboratory, a second sample of the residual exudate covering the ulcer was taken from the patient for a post-treatment follow-up microscopy after Congo red negative staining. Only very rare cocci were found with great efforts. Inoculation of 0.1 ml of the morning sample of the saliva on the surface of a blood agar plate showed more than 3,000 bacterial colonies growing, similar to those observed in FIG. 1.

The canker sores of all six patients healed completely after a four days course of medication. No more antibiotics were given thereafter.

On day 6, i.e. two days after the last dose of medication, the patients were instructed to collect a sample of saliva in a sterile test tube upon waking up in the morning before brushing their teeth. The saliva was brought to the laboratory. Aliquot of 0.1 ml of each saliva sample was pipetted and inoculated on the surface of a blood agar plate and incubated aerobically as described previously. After 18 hours of incubation, there were more 3,000 colonies growing on each blood agar plate. The overwhelming majority of the colonies were those of Neisseriae and non-β-hemolytic streptococci, similar to those observed in FIG. 1.

The results of this series of studies indicate that the inhibitory effects of 50 mg penicillin G potassium on the bacterial growth of the oral flora are not long-lasting and the oral flora are not permanently altered by this intermittent high concentration of penicillin treatment. The normal oral flora was demonstrated during the four-day period of medication and two days after the medication was completed. This type of high concentration of topical antibiotic treatment produces an intermittent total inhibition of bacterial growth in the saliva and perhaps also in the lesion of the superficial canker ulcers. The disruption of the synergistic effects of a group of opportunistic pathogens on an established superficial inflamed ulcer may create an unfavorable environment for these organisms to continue to multiply on the surface of the lesion.

Example VII
Local concentrations of penicillin in saliva after topical medication of various doses of penicillin G potassium Five healthy adult volunteers, three men and two women, were selected for this study. The same volunteers were used as the subjects for three studies, and the results are summarized as follows.

On the day of study, two hours after breakfast, the volunteers were given a dose of 100 mg, 50 mg, 20 mg, 10 mg and 2 mg of USP grade penicillin G potassium powder respectively. The drug powder was placed in the right oral sulcus between the lower gum and the buccal mucosa to be dissolved in a minimum amount of saliva. This loculated pocket of saliva was not to be swallowed and was not to be further diluted by saliva from other parts of the mouth for one hour. At 6 minutes, 20 minutes, 40 minutes and 60 minutes after drug application, an aliquot of 0.01 ml was taken from this pocket of saliva and added into a test tube containing 10 ml of nutrient broth to give a 1,000 times dilution. After being mixed well, aliquots of the mixtures of saliva sample and nutrient broth were forced to pass through bacterial filters into sterile test tubes. Then 0.8 ml of each 1:1,000 diluted filtrate was pipetted and added to 3.2 ml of nutrient broth to make an additional 5 times dilution in a total volume of 4 ml. Two ml was pipetted from the latter to make a serial double dilution of saliva sample in 2 ml of nutrient broth, as described above under a., in 12 test tubes. The dilution factor for the saliva sample in test No. 1 was 1:5,000 and increased progressively to 1:10,240,000 in test tube No. 12.

After the 60-minute sample was taken, the subjects were given an 8 oz. glass of water to drink or to rinse his or her mouth, but refrained from drinking and eating for another hour. At the end of this last hour, i.e. about 2 hours after the drug application, another saliva sample of 0.2 ml was withdrawn and added to 3.8 ml of nutrient broth to make a 1:20 dilution and the mixture was forced to pass a bacterial filter into a sterile test tube. Two (2) ml of the filtrate was pipetted from this 1:20 diluted mixture for antibiotic activity assays.

Each filtered mixture in test tube was inoculated with 0.1 ml of a 1:1,000 dilution of a 12 hour broth culture of *Staphylococcus aureus* ATCC 29213.

A row of 6 test tubes each containing 2 ml of nutrient broth with decreasing concentrations of penicillin G potassium from 6.2 to 0.16 mcg/ml, using a serial double dilution method described in a., was prepared and similarly inoculated with 0.1 ml broth culture of *Staphylococcus aureus* ATCC 29213 as the standard.

All test tubes were incubated at 37° C. for 18 hours and observed for bacterial growth against an inoculated broth containing neither antibiotic nor saliva samples.

The results showed that *Staphylococcus aureus* ATCC 29213 consistently presented with an MIC of 0.75 mcg/ml of penicillin G potassium throughout the three studies. It failed to grow in the nutrient broth containing penicillin at this concentration or higher in the standard row of 6 test tubes, but grew in the tubes containing 0.37 mcg/ml penicillin (or less) to full turbidity similar to that observed in the positive control. The test tube of the highest number with the highest dilution factor of saliva in nutrient broth in which no bacterial growth was observed was interpreted as containing an equivalent of penicillin G potassium at 0.75 mcg/ml. Using the dilution factors, it was calculated that, after topical application of 2 to 100 mg of penicillin G potassium dry powder, the concentrations of penicillin G potassium in the saliva at the site of medication within the first hour and one hour after purging the mouth with water were as follows.

TABLE 6

Penicillin G Potassium Concentrations in mg/ml in Saliva after Topical Application

| Penicillin powder, mg applied | Penicillin concentration in saliva mg/ml | | | | 120 min mcg/ml |
|---|---|---|---|---|---|
| | 6 min | 20 min | 40 min | 60 min | |
| 100 (study 1) | 960 | 240 | 30 | 15 | (<15) |
| 100 (study 2) | 480 | 240 | 60 | 30 | (<15) |
| 100 (study 3) | 480 | 120 | 30 | 15 | (<15) |
| 50 (study 1) | 480 | 240 | 30 | 7.5 | (<15) |
| 50 (study 2) | 240 | 120 | 15 | 7.5 | (<15) |
| 50 (study 3) | 480 | 240 | 30 | 7.5 | (<15) |
| 20 (study 1) | 120 | 60 | 7.5 | 7.5 | (<15) |
| 20 (study 2) | 240 | 60 | 7.5 | 7.5 | (<15) |
| 20 (study 3) | 120 | 30 | 15 | 7.5 | (<15) |
| 10 (study 1) | 60 | 30 | 15 | 3.75 | (<15) |
| 10 (study 2) | 60 | 30 | 7.5 | 3.75 | (<15) |
| 10 (study 3) | 30 | 15 | 7.5 | 7.5 | (<15) |
| 2 (study 1) | 15 | 7.5 | 3.75 | <3.75 | (<15) |
| 2 (study 2) | 7.5 | <3.75 | <3.75 | <3.75 | (<15) |
| 2 (study 3) | 7.5 | <3.75 | <3.75 | <3.75 | (<15) |

<3.75 = lower than 3.75 mg/ml. On the right column (<15) = lower than 15 mcg/ml.

The results of this study showed that the initial peak concentrations of penicillin G potassium can be achieved at the site of medication to the levels 7.5–960 mg/ml when doses of 2 mg to 100 mg of drug powder were applied to the oral pouch. But the concentration of antibiotic drops rapidly over the period of 60 minutes. When 2 mg was selected as the dose, it dropped down to below 3.75 mg/ml in 20 minutes in the saliva in two of three subjects. Since 2 mg/ml of penicillin was required to produce a total inhibition of bacterial growth in the saliva with certainty in vitro, as demonstrated above, no attempts were made to titrate the concentrations below 3.75 mg/ml which is considered a near threshold concentration of 2 mg/ml penicillin G potassium (in a serial double-dilution study as designed) in saliva for total bacterial growth inhibition.

In order to maintain a sustained concentration of a minimum 3.75 mg/ml of penicillin in the saliva at the site of medication for one hour, at least 10 mg of penicillin G potassium in the form of dry powder is required, even under strictly controlled conditions. Therefore, to insure adequate margins of antibacterial efficacy, 50 mg of penicillin G potassium dry powder is chosen as the single dose of medication.

The results of this study also indicate that Penicillin G potassium is eliminated quickly from the saliva when the test subject or patient is allowed to resume normal food intake or to drink liquids. The concentration of the drug in the saliva dropped down to below the detectable level of 15 mcg/ml designed for this study one hour after the test subjects drank 8 oz. of fluid.

Example VIII

Concentrations of penicillin G potassium in saliva after an oral ingestion of 250 or 500 mg of the drug substance Eight healthy adults, four men and four women, volunteered for this study. Two men and two women were given 500 mg each, and two men and two women were given 250 mg of USP grade penicillin G potassium powder each by mouth, respectively. These two doses were chosen for the study because they have been used as the standard adult oral doses for systemic treatment of human bacterial infections.

In this study, the drug powder was suspended in one teaspoonful of water and swallowed by the test subjects two hours after breakfast, followed by drinking an 8 Oz. glass of water. The test subjects refrained from drinking or eating for the next three hours. Six samples of saliva were collected from each subject at 30-minute intervals in succession in the next three hours. An aliquot of 0.2 ml from each saliva sample was transferred to 3.8 ml of nutrient broth. The mixture of the latter was forced to pass a bacterial filter. Two (2) ml of the bacteria-free filtrate was pipetted out into a sterile test tube and inoculated with 0.1 ml of a 1:1,000 dilution of a 12 hours broth culture of *Staphylococcus aureus* ATCC 29213 and incubated at 37° C. for 18 hours. A series of test tubes containing known concentrations, from 6.2 mcg/ml to 0.16 mcg/ml, of penicillin G potassium in 2 ml of nutrient broth was also inoculated with the same broth culture as standards.

After 18 hours of incubation, the inoculated *Staphylococcus aureus* did not show evidence of growth in the tubes containing 0.75 mcg or more of penicillin G potassium per ml of nutrient broth. All 48 test tubes containing saliva-broth filtrate inoculated with the same Staphylococcus broth culture showed vigorous bacterial growth. Since 0.75 mcg/ml is the consistent MIC observed in this laboratory for *Staphylococcus aureus* ATCC 29213, the penicillin concentration in the saliva-broth filtrate must have been at a level below 0.75 mcg/ml.

Taking the dilution factor of 0.2 ml of saliva sample and 3.8 ml of nutrient broth in the mixture filtrates into consideration, it is concluded that the concentration of penicillin G potassium in the human saliva did not reach the level of 15 mcg/ml after an oral ingestion of 250 mg or 500 mg of penicillin G potassium.

Example IX

Local concentrations of penicillin in saliva after topical medication of the drug formulation, penicillin G potassium 50 mg tablet Five healthy adult volunteers, three men and two women, were selected for this study. The drug product was the formulation of penicillin G potassium, 50 mg, containing excipients such as 1 mg magnesium stearate, 0.6 mg of stearic acid, 7.5 mg of lactose and other inactive binding agents in a total weight of 73 mg per troche.

On the day of study, two hours after breakfast, the volunteers were given a single tablet of the drug, placed in the right oral sulcus between the lower gum and the buccal mucosa to be dissolved in a minimum amount of saliva in about six (6) minutes. This loculated pocket of saliva was not to be swallowed and was not to be further diluted by saliva from other parts of the mouth for one hour. At 6 minutes, 20 minutes, 40 minutes and 60 minutes after drug application, an aliquot of 0.01 ml was aspirated from this pocket of saliva and added into a test tube containing 10 ml of nutrient broth to give a 1,000 times dilution. After being mixed well, aliquots of the mixtures of saliva sample and nutrient broth were forced to pass through bacterial filters into sterile test tubes. Then 0.8 ml of each 1:1,000 diluted filtrate was pipetted and added to 3.2 ml of nutrient broth to make an additional 5 times dilution in a volume of 4 ml. Two ml was pipetted from the latter to make a serial double dilution of saliva sample in 2 ml of nutrient broth, as described above under a, in 12 test tubes. The dilution factor for the saliva sample in test No. 1 was 5,000 and decreased progressively to 1:10,240,000 in test tube No.12.

Each filtered mixture in test tube was inoculated with 0.1 ml of a 1:1,000 dilution of a 12 hour broth culture of *Staphyloccus aureus* ATCC 29213.

A row of 6 test tubes each containing 2 ml of nutrient broth with decreasing concentrations of penicillin G potassium, USP Reference Standard 502508, at 6.2, 3.1, 1.5, 0.75, 0.32, and 0.16 mcg/ml, using a serial double dilution method described in a., was prepared and similarly inoculated with 0.1 ml broth culture of *Staphyloccus aureus* ATCC 29213 as the standard.

All test tubes were incubated at 37° C. for 18 hours and observed for bacterial growth against an inoculated broth containing neither antibiotic nor saliva samples.

The results showed that the MIC of *Staphylococcus aureus* ATCC 29213 was 0.75 mcg/ml of penicillin G potassium. The test tube of highest number with the highest dilution factor of saliva in nutrient broth in which no bacterial growth was observed was interpreted as containing an equivalent of penicillin G potassium at 0.75 mcg/ml. Using the dilution factors, it was calculated that, after topical application of the drug product, the concentrations of penicillin G potassium in the saliva at the site of medication within the first hour were as follows.

TABLE 7

Penicillin G Potassium Concentrations in mg/ml in Saliva after Drug Application

|       | 6 min   | 20 min  | 40 min | 60 min |
|-------|---------|---------|--------|--------|
| Conc. | 240–480 | 120–240 | 30–60  | 7.5–15 |

These results indicate that the drug product of penicillin G potassium 50 mg tablet, provides adequate levels of antibiotic concentration for a total bacterial growth inhibition during the one-hour medication time.

Example X

Minimal total inhibition concentration of tetracyclines for human salivary microbial flora Source of human salivary flora: undiluted saliva freshly collected from the mouth of a healthy adult who had refrained from fluid or food intake for three hours after breakfast prior to saliva collection.

Antibacterial agent: Doxycycline cyclate (a tetracycline) for injection USP, equivalent to 100 mg Doxycycline (Fugusawa USA, Inc., Deerfield, IL 60015-2548. Procedure:

1) An adequate amount of saliva was added to the vial of doxycycline to make a total volume of suspension of 3.1 ml, equivalent to a 32 mg/ml concentration of the antibacterial agent.
2) An aliquot of 0.2 ml of the 32 mg/ml doxycycline salivary solution was pipetted out for serial double dilutions in saliva in test tubes to the final concentrations of 32, 16, 8, 4, 2, 1, 0.5, 0.25 and 0.12 mg of doxycycline per ml.
3) All tubes containing saliva with different concentrations of doxycycline were incubated in 37 degrees Celsius for one hour.
4) At the end of the one-hour incubation, 0.1 ml of the salivary doxycycline solution was pipetted from each test tube and inoculated on the surface of a blood agar plate. An aliquot of 0.1 ml saliva sample containing no antibacterial agent was spread on the surface of a blood agar plate as control.
5) After 18 hours of incubation in 37 degrees Celsius aerobically, the growth on the blood agar plates was inspected and compared for the presence or absence of bacterial colonies.

Figure 12:
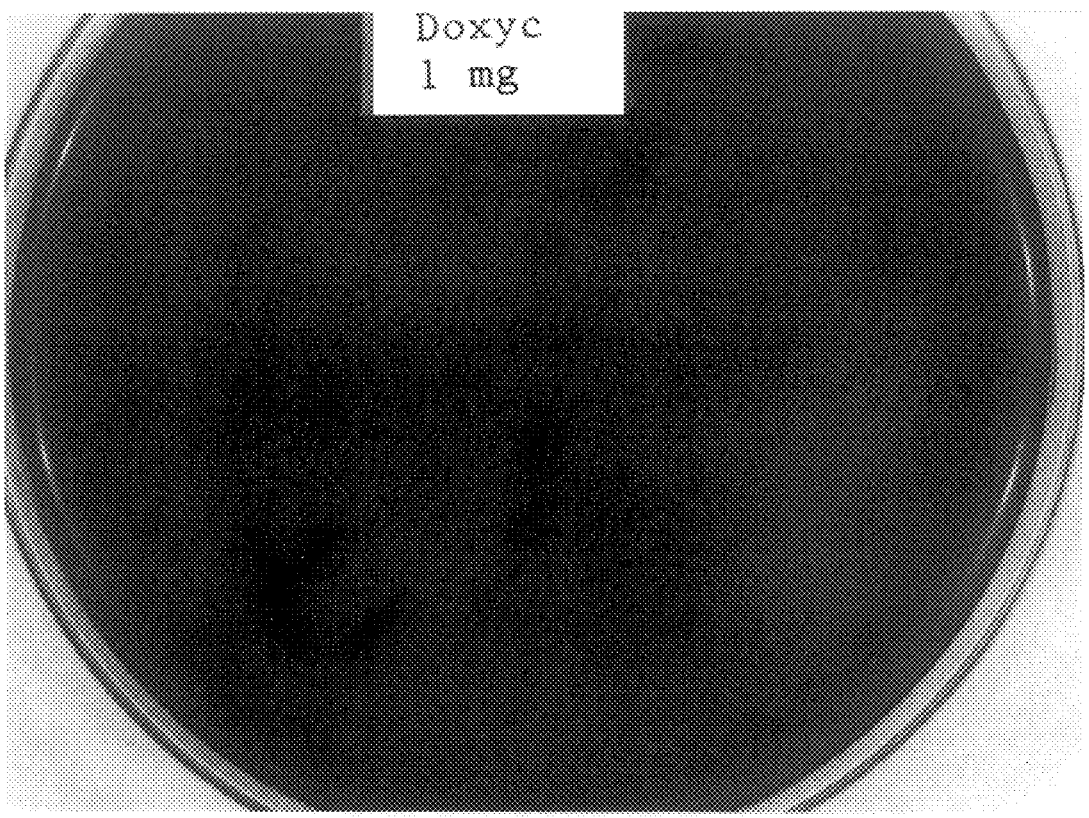
FIG. 12 All bacteria in the 0.1 ml sample of saliva were either destroyed or totally inhibited by doxycycline at a concentration of 1 ml/ml or above.
Figure 13:
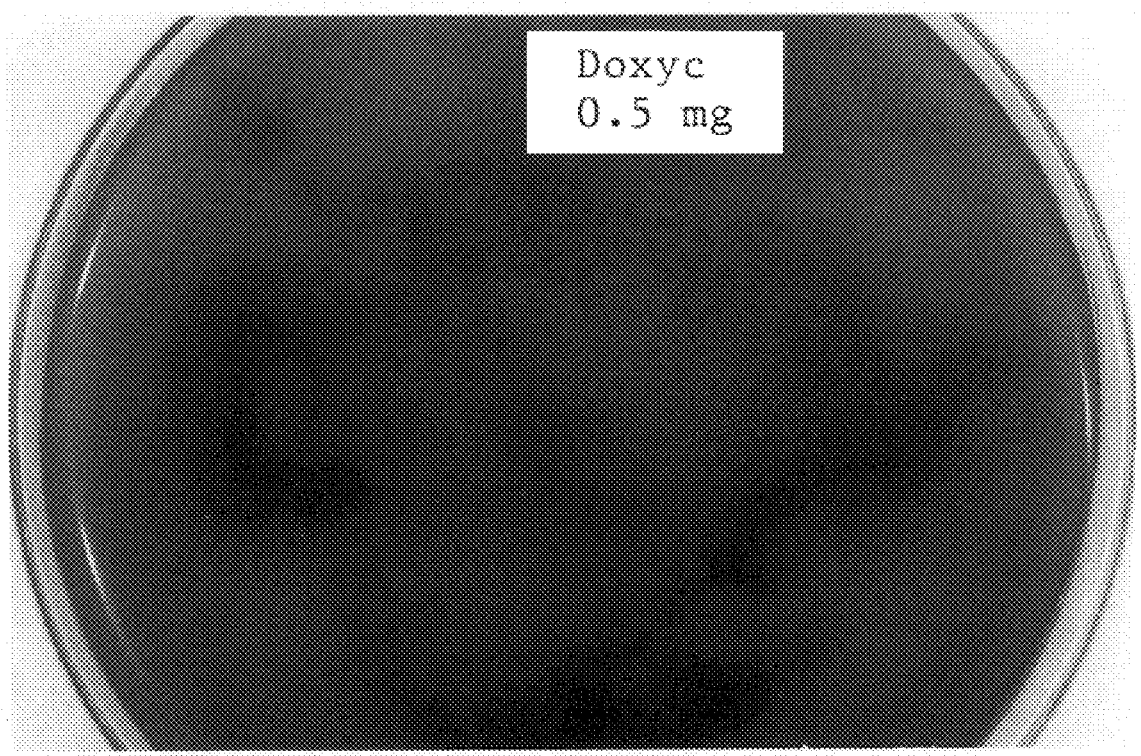
FIG. 13 A few surviving or uninhibited bacteria grew into colonies at the periphery of the 0.1 ml salivary inoculum where the doxycycline concentration dropped down to 0.5 mg/ml in the saliva.
Figure 14:
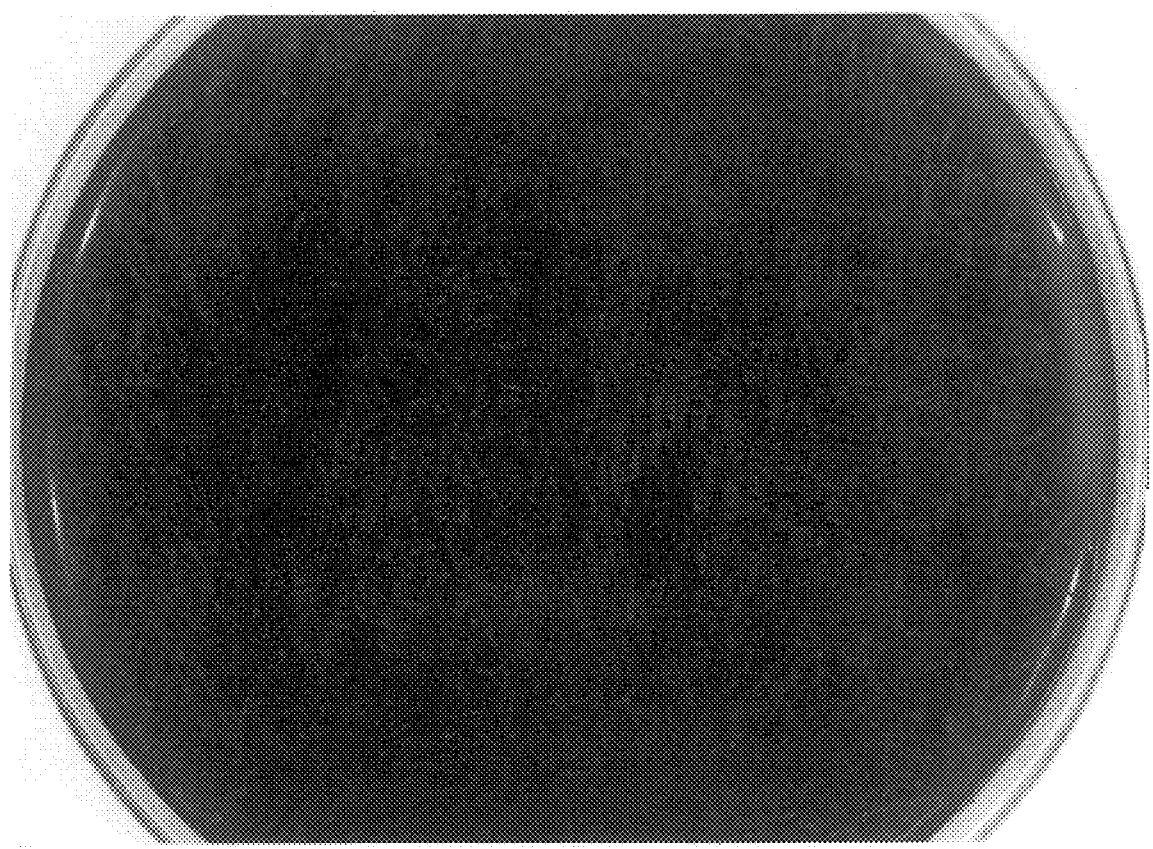
FIG. 14 Saliva, 0.1 ml. Inoculated on the surface of a blood agar plate and incubated aerobically at 37° C. for 18 hours. The culture is dominated by colonies of Neisseriae and non-β-hemolytic streptococci.

Results: No bacterial colonies were observed on the surface of the blood agar plates inoculated with saliva containing 1 mg/ml (FIG. 12), 2 mg/ml, 4 mg/ml, 8 mg/ml, 16 mg/ml, 32 mg/ml of doxycycline. Varying numbers of bacterial colonies were observed on the agar plates inoculated with saliva containing 0.5mg/ml (FIG. 13), 0.25 mg/ml and 0.12 mg/ml of doxycycline. The control plate was fully covered with highly crowded bacterial colonies (FIG. 14).

Conclusion: The minimal total inhibition concentration of doxycycline hyclate is about 1 mg/ml for the human salivary microbial flora.

Based on published literature, after an oral ingestion of 100 of doxycycline hyclate in fasting adults, a peak serum concentration of 1.5–2.1 ug/ml is achieved; after 200 mg, the peak levels can reach 2.6–3 ug/ml. Intravenous injection of 100 mg and 200 mg of doxycycline hyclate results in peak serum level of 2.5 ug/ml and 2.6 ug/ml, respectively. All are below the minimal total inhibition concentration for human salivary microbial flora.

Example XI

Minimal Total inhibition concentration of ciprofloxacin for human salivary microbial flora Source of human salivary flora: undiluted saliva freshly collected from the mouth of a healthy adult who had refrained from fluid or food intake for three hours after breakfast prior to saliva collection.

Antibacterial agent: Cipro (a member of the quinolone group) I.V. 200 mg in 20 ml (1%) for intravenous infusion. Inactive ingredients: lactic acid as stabilizer, HCL to adjust pH and water. Division Bayer Corporation. Procedure:

1) An aliquot of 1 ml of the Cipro solution, 1%, was added to 1.5 ml to make a total volume of 2.5 ml, equivalent to a 4 mg/ml concentration of the antibacterial agent in saliva.
2) An aliquot of 0.2 ml of the 4 mg/ml Cipro salivary solution was pipetted out for serial double dilutions in saliva in test tubes to the final concentrations of 4, 2, 1, 0.5, 0.25 and 0.12 mg of Cipro per ml, respectively.
3) All tubes containing saliva with different concentrations of Cipro were incubated in 37 degrees Celsius for one hour.
4) At the end of the one-hour incubation, 0.1 ml of the salivary Cipro solution was pipetted from each test tube and inoculated on the surface of a blood agar plate. An aliquot of 0.1 ml saliva sample containing no Cipro was spread on the surface of a blood agar plate as control.
5) After 18 hours of incubation in 37 degrees Celsius aerobically, the growth on the blood agar plates was inspected and compared for the presence or absence of bacterial colonies.

Figure 15:
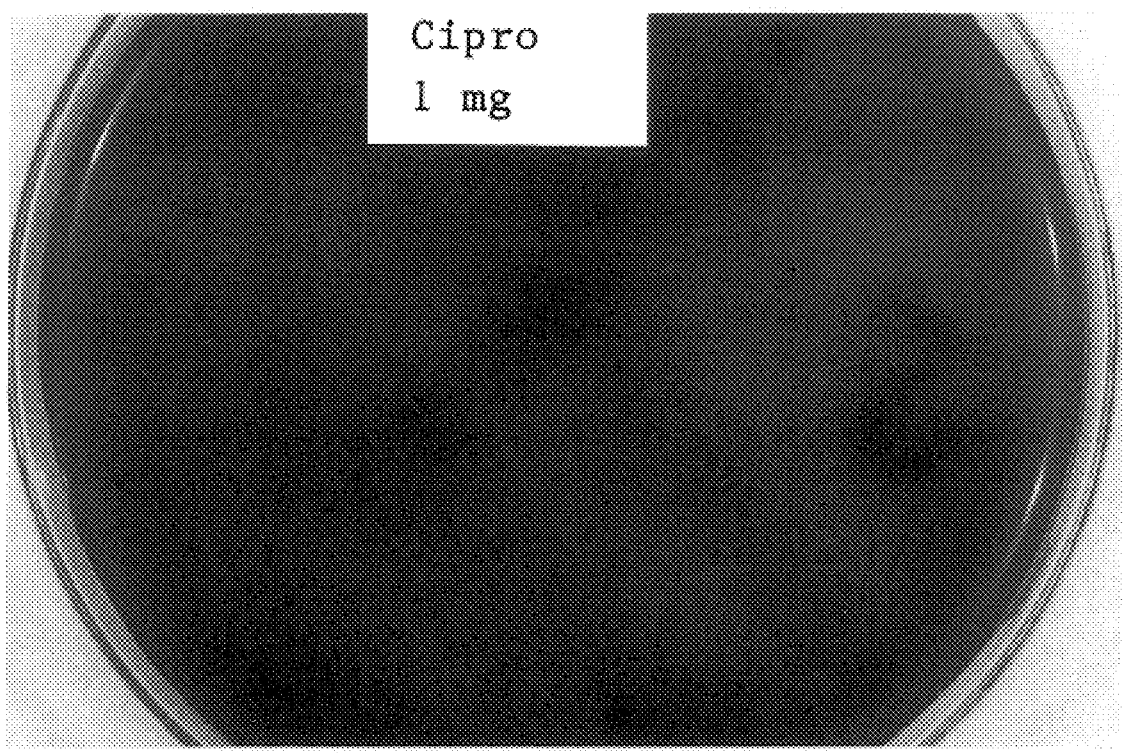
FIG. 15 All bacteria in the 0.1 ml sample of saliva were either destroyed or totally inhibited by ciprofloxacin at a concentration of 1 ml/ml or above.
Figure 16:
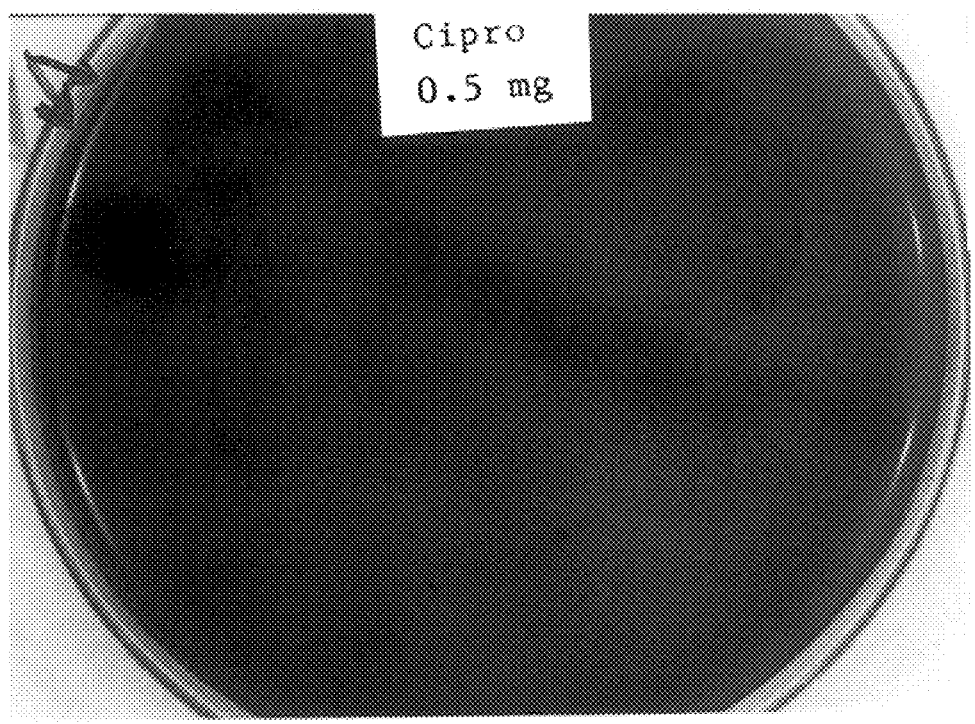
FIG. 16 A few surviving or uninhibited bacteria grew into colonies at the periphery of the 0.1 ml salivary inoculum where the ciprofloxacin concentration dropped down to 0.5 mg/ml in the saliva.
Figure 17:
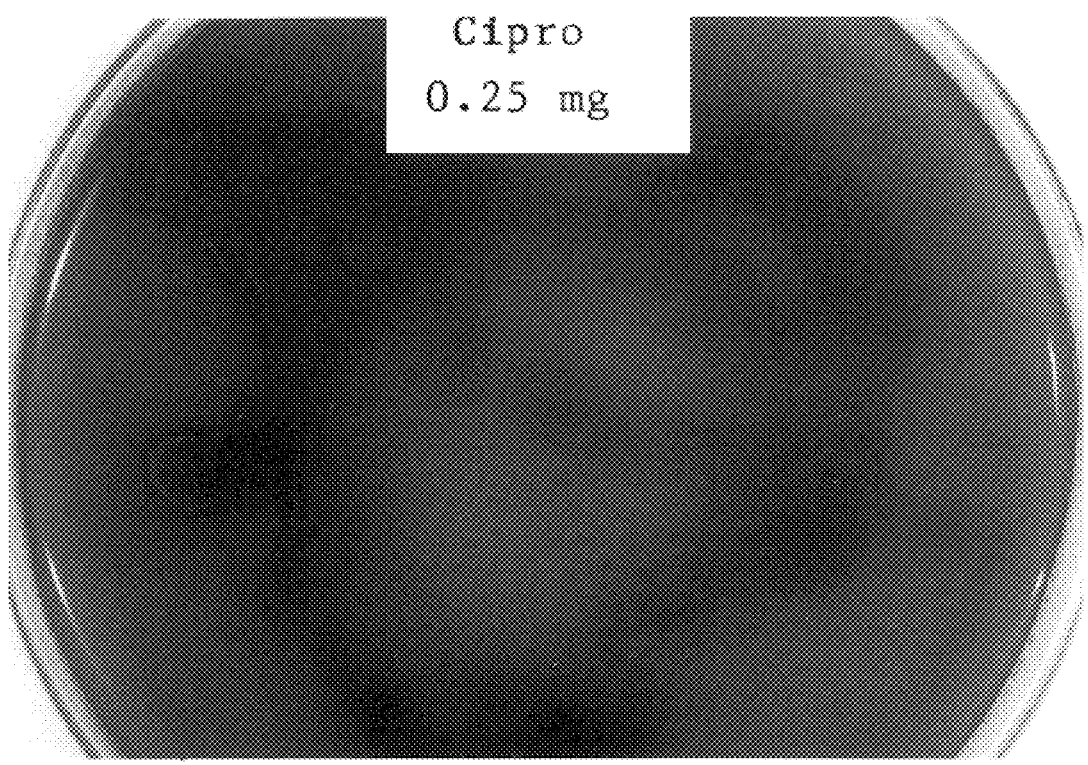
FIG. 17 Progressively more surviving or uninhibited bacteria grew into colonies at the periphery of the salivary inoculum where the ciprofloxacin concentration lo dropped down to 0.25 mg/ml.

Results: No bacterial colonies were observed on the surface of the blood agar plates inoculated with saliva containing 1 mg/ml (FIG. 15), 2 mg/ml, and 4 mg/ml of Cipro. Varying numbers of bacterial colonies were observed on the agar plates inoculated with saliva containing 0.5mg/ml (FIG. 16), 0.25 mg/ml (FIG. 17) and 0.12 mg/ml of Cipro. The control plate was fully covered with highly crowded bacterial colonies (FIG. 14).

Conclusion: The minimal total inhibition concentration of Cipro is about 1 mg/ml for the human salivary microbial flora.

Based on published literature, after an oral ingestion of 250 mg, 500 mg or 1000 mg of ciprofloxacin in healthy fasting adults, a peak serum concentration of 0.76–1.5, 1.6–2.9, 2.5–4.3 or 3.4–5.4 ug/ml is achieved. Following intravenous injection of 200 mg or 400 mg of cyprofloxacin results in peak serum level of 2.1 ug/ml and 4.6 ug/ml, respectively, immediately after infusion. All are below the minimal total inhibition concentration for human salivary microbial flora.

All supporting books cited in this specification, as well as any articles or other references cited hereinabove, are incorporated herein by reference in their entirety.

While the present invention has been described in connection with what is presently considered to be practical and preferred embodiments, it is understood that the present invention is not limited or restricted to the disclosed embodiments but, on the contrary, is intended to cover various modifications and equivalent arrangements included within the spirit and scope of the appended claims.

Thus, it is to be understood that variations in the described invention will be obvious to those skilled in the art without departing from the novel aspects of the present invention and such variations are intended to come within the scope of the claims.

What is claimed is:

1. A method of treating bacterial infections in the oral mucosa comprising directly topically administering in dry fonn a composition comprising
   a) an effective amount of a dry dosage of an antibacterial agent to achieve a concentration of at least 1 mg/ml of the antibacterial agent in saliva of a person treated therewith, which antibacterial agent is selected from the group consisting of penicillins, beta-lactam antibiotics, tetracyclines aminoglycosides, cephalosporins, macrolides, vancomycin, bacitracin, chloramphenicol, qulinolones, sulfonamides, nitrofurans, and their salts and mixtures thereof,
   b) optionally, an effective amount of a salt or oxide of a polyvalent metal compound selected from the group consisting of magnesium, zinc, calcium, aluminum, bismuth, titanium and copper and mixtures thereof; and
   c) optionally, binding agents.

2. The method according to claim 1, wherein the infections of the oral mucosa are selected from the group consisting of one or more of gum disease, periodontal infection, stornatitis and gingivitis.

3. The method according to claim 1, wherein the composition delivers directly to the infection a dosage concentration level of the antibacterial agent which is substantially higher in comparison to dosage concentrations levels achieved if the antibacterial agent is delivered to the infection through blood by conventional gastrointestinal absorption, intramuscular or intravenous injection of the antibacterial agent.

4. The method according to claim 1, wherein the dry dosage of antibacterial agent is in the amount between about 2–200 mg.

5. The method according to claim 1, wherein the dry dosage of antibacterial agent is in the amount of about 50 mg.

6. The method according to claim 1, wherein the composition is maintained topically on the site of the infection for at least about 5 minutes.

7. The method according to claim 1, wherein the amount of dry dosage is effective to achieve a concentration of at least 2 mg/ml of the antibacterial agent in saliva.

8. The method according to claim 1, wherein the composition is administered at least four times daily.

9. The method according to claim 1, wherein the composition is in the form of a troche.

10. The method according to claim 1, wherein the composition is in the form of a powder.

11. The method according to claim 1, wherein the antibacterial agent is penicillin.

12. The method according to claim 11, wherein the penicillin is penicillin G.

13. The method according to claim 1, wherein the antibacterial agent is tetracycline.

14. The method according to claim 1, wherein the composition comprises penicillin and magnesium stearate.

15. The method according to claim 1, wherein the binding agents include one or more polymeric binding agents.

16. The method according to claim 15, wherein the polymeric binding agents include one or more of methyl cellulose, ethyl cellulose hydroxycellulose, polyvinylpyrrolidone, gums, starches, lactose, sucrose, and mixtures thereof.

17. The method according to claim 1, wherein the amount of polyvalent metal compound in the composition is between about 0.2–5 mg.

18. The method according to claim 14, wherein the amount of penicillin in the composition is about 50 mg and the amount of magnesium stearate is about 1.0 mg.

* * * * *